(12) United States Patent
Candau et al.

(10) Patent No.: US 8,999,299 B2
(45) Date of Patent: Apr. 7, 2015

(54) PHOTOPROTECTIVE COSMETIC COMPOSITIONS COMPRISING SILICON-CONTAINING S-TRIAZINE COMPOUNDS SUBSTITUTED WITH TWO AMINOBENZOATE OR AMINOBENZAMIDE GROUPS AND NON-SILICON-CONTAINING LIPOPHILIC TRIAZINE COMPOUND UV-SCREENING AGENTS

(75) Inventors: Didier Candau, Bievres (FR); Herve Richard, Les Pavillons sous Bois (FR)

(73) Assignee: L'Oreal, Paris (FR)

( * ) Notice: Subject to any disclaimer, the term of this patent is extended or adjusted under 35 U.S.C. 154(b) by 419 days.

(21) Appl. No.: 11/987,213

(22) Filed: Nov. 28, 2007

(65) Prior Publication Data

US 2008/0138303 A1    Jun. 12, 2008

Related U.S. Application Data

(60) Provisional application No. 60/873,564, filed on Dec. 8, 2006.

(30) Foreign Application Priority Data

Nov. 28, 2006  (FR) .................................... 06 55166

(51) Int. Cl.
*A61K 8/00*     (2006.01)
*A61K 8/49*     (2006.01)
*A61Q 17/04*    (2006.01)

(52) U.S. Cl.
CPC .............. *A61K 8/4966* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 4,724,137 A | 2/1988 | Hoppe et al. | |
| 5,955,060 A | 9/1999 | Huglin et al. | |
| 6,018,044 A * | 1/2000 | Huber | 544/197 |
| 6,096,294 A | 8/2000 | Hansenne et al. | |
| 6,423,302 B1 | 7/2002 | Gers-Barlag et al. | |
| 6,514,485 B1 | 2/2003 | Malpede et al. | |
| 6,517,742 B1 * | 2/2003 | Richard et al. | 252/401 |
| 7,014,842 B2 | 3/2006 | Dueva-Koganov et al. | |
| 2005/0013782 A1 * | 1/2005 | Goppel et al. | 424/59 |

FOREIGN PATENT DOCUMENTS

| | | |
|---|---|---|
| EP | 0 517 104 A1 | 12/1992 |
| EP | 0 570 838 A1 | 11/1993 |
| EP | 0 775 698 A1 | 3/1997 |
| EP | 0 841 341 A1 | 5/1998 |
| EP | 0 933 376 B1 | 8/1999 |
| EP | 1 034 778 A2 | 9/2000 |
| EP | 1 180 360 A2 | 2/2002 |
| EP | 1 582 201 A2 | 10/2005 |
| JP | H10-139648 | 5/1998 |
| JP | H10-175836 | 6/1998 |
| JP | H10-175837 | 6/1998 |
| JP | 2000-063388 | 2/2000 |
| JP | 2005-239722 | 9/2005 |
| JP | 2007-509889 | 4/2007 |
| WO | WO 02/17873 | 3/2002 |

OTHER PUBLICATIONS

English translation of Notice of Reasons for Rejection in Japanese Patent Application 2007-306935 (Feb. 5, 2013).
English translation of Notice of Reasons for Rejection in Japanese Patent Application 2007-306935 (Nov. 19, 2013).

* cited by examiner

*Primary Examiner* — Johann R Richter
*Assistant Examiner* — David Browe
(74) *Attorney, Agent, or Firm* — Buchanan Ingersoll & Rooney PC

(57) ABSTRACT

UV-photoprotective, topically applicable cosmetic/dermatological compositions contain:
(a) at least one silicon-containing s-triazine substituted with two aminobenzoate or aminobenzamide groups of specific formula (I),

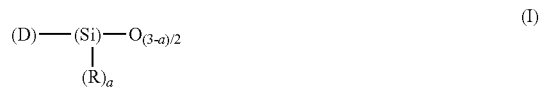

and (b) at least one non-silicon-containing lipophilic 1,3,5-triazine compound UV-screening agent, such compositions having improved photoprotective effectiveness in the UV-B range and the 1,3,5-triazine compound(s) being improvedly soluble therein.

31 Claims, No Drawings

PHOTOPROTECTIVE COSMETIC COMPOSITIONS COMPRISING SILICON-CONTAINING S-TRIAZINE COMPOUNDS SUBSTITUTED WITH TWO AMINOBENZOATE OR AMINOBENZAMIDE GROUPS AND NON-SILICON-CONTAINING LIPOPHILIC TRIAZINE COMPOUND UV-SCREENING AGENTS

CROSS-REFERENCE TO PRIORITY/PROVISIONAL APPLICATIONS

This application claims priority under 35 U.S.C. §119 of FR 06/55166, filed Nov. 28, 2006, and of U.S. Provisional Application No. 60/873,564, Dec. 8, 2006, each hereby expressly incorporated by reference and each assigned to the assignee hereof.

BACKGROUND OF THE INVENTION

1. Technical Field of the Invention

The present invention relates to sunscreen compositions comprising, formulated into a cosmetically acceptable carrier, at least one UV-screening system including the combination of at least one silicon-containing S-triazine substituted with two aminobenzoate or aminobenzamide groups of formula (I) or one of its tautomeric forms, more fully described below, and of at least one non-silicon-containing lipophilic 1,3,5-triazine-type UV-screening agent.

2. Description of Background and/or Related and/or Prior Art

Light radiation with wavelengths from 280 nm to 400 nm is known to brown the human epidermis; more particularly, rays with a wavelength in the range 280 to 320 nm, known as UV-B, are known to cause erythema and cutaneous burns which may be deleterious to the development of a natural tan. For these reasons and for aesthetic reasons, there is a constant demand for means for controlling this natural tanning for the purpose of thus controlling the color of the skin; it is therefore advisable to screen out this UV-B radiation.

It is also known that UV-A rays with wavelengths in the range 320 to 400 nm, which cause the skin to brown, are capable of inducing an impairment of said skin, in particular in the case of sensitive skin or skin continually exposed to solar radiation. In particular, UV-A rays cause a loss of elasticity of the skin and the appearance of wrinkles, resulting in premature aging of the skin. These promote the triggering of the erythematous reaction or amplify this reaction in certain individuals and can even be responsible for phototoxic or photoallergic reactions. Thus, for aesthetic and cosmetic reasons, such as preservative the natural elasticity of the skin, for example, more and more individuals seek to control the effect of UV-A rays on their skin. It is therefore desirable to also screen out the UV-A radiation.

With the goal of ensuring protection of the skin and keratin materials against UV radiation, anti-sun/sunscreen compositions comprising organic screening agents that are active in the UV-A range and active in the UV-B range are generally used. The majority of these screening agents are liposoluble.

Many cosmetic compositions useful for photoprotection (UV-A and/or UV-B) of the skin have been proposed to date.

These anti-sun/sunscreen compositions are topically in the form of an oil-in-water or water-in-oil emulsion, of gels or of anhydrous products which contain, at various concentrations, one or more organic and/or inorganic screening agents. These screening agents and the amounts thereof are selected according to the desired protection factor.

Depending on their lipophilic or, on the contrary, hydrophilic nature, these screening agents can be distributed, respectively, either into the fatty phase or into the aqueous phase of the final composition.

Screening agents that are particularly advantageous and currently widely used are non-silicon-containing lipophilic 1,3,5-triazine-type screening agents. These compounds are known in cosmetics for their absorbent properties with respect to UV radiation, and more particularly UV-B rays. They are described in EP-A-0,517,104, EP-A-0,570,838, EP-A-0,796,851 and EP-A-0,775,698. The 2,4,6-tris[p-(2'-ethylhexyl-1'-oxycarbonyl)anilino]-1,3,5-triazine derivative marketed in particular under the trademark "Uvinul T 150" by BASF, the 2-[(p-tert-butylamido)anilino]-4,6-bis[(p-(2'-ethylhexyl-1'-oxycarbonyl)anilino]-1,3,5-triazine or "Diethylhexyl Butamido Triazone" (INCI name) marketed under the trademark "Uvasorb HEB" by Sigma 3V, and the 2,4-bis{[4, 2-ethylhexyloxy)]-2-hydroxy]phenyl}-6-(4-methoxyphenyl)-1,3,5-triazine derivative marketed under the trademark "Tinosorb S" by Ciba are in particular known.

These are lipophilic screening agents which are active in the UV-B range but which have the particularity and also the disadvantage of being solid at ambient temperature. As a result, their use in an anti-sun/sunscreen cosmetic composition implies certain constraints in terms of their formulation and their use, in particular when it comes to finding solvents that make it possible to properly solubilize them. Furthermore, the activity in the UV-B range of these screening agents used alone is limited.

It is known that cinnamate derivatives such as 2-ethylhexyl 4-methoxycinnamate or isoamyl 4-methoxycinnamate are good solvents for UV-screening agents that are difficult to solubilize in oils, and have good photoprotective properties in the UV-B range. However, these cinnamate derivatives have the drawback of having insufficient photostability and of disturbing the photostability of the complete screening systems into which they are introduced, and in particular those containing dibenzoylmethane derivatives.

It is also known that alkyl $\beta,\beta'$-diphenyl acrylate or $\alpha$-cyano $\beta,\beta'$-diphenyl acrylate derivatives are photostable and are good solvents for lipophilic UV-screening agents that are difficult to solubilize in oils, but their absorbent capacity in the UV-B range is highly insufficient.

SUMMARY OF THE INVENTION

It has now surprisingly been discovered that the use of a screening agent of the type silicon-containing s-triazine substituted with two aminobenzoate or aminobenzamide groups of formula (I) or one of its tautomeric forms, more fully described below, in combination with a non-silicon-containing lipophilic 1,3,5-triazine-type screening agent makes it possible to solve or ameliorate the disadvantages and drawbacks indicated above.

Indeed, the use of a screening agent of the type silicon-containing s-triazine substituted with two aminobenzoate or aminobenzamide groups of formula (I) makes it possible, first, to improve the solubility of the non-silicon-containing lipophilic 1,3,5-triazine-type screening agents in the normal solvents included in anti-sun formulations and, secondly, to obtain better photoprotective effectiveness in the UV-B range. Such use also makes it possible to substantially reduce the phenomena of photodegradation of the other screening agents of the composition caused by the presence of certain types of solubilizing liquid UV-B-screening agents, such as cinnamate derivatives.

The anti-sun/sunscreen compositions containing such a combination of organic UV-screening agents also exhibits good persistence with respect to water, to perspiration and to washing, and also good persistence over time.

These discoveries constitute the basis of the present invention.

Thus, the present invention features compositions comprising, formulated into a cosmetically acceptable carrier, at least one UV-screening system, which comprises:

a) at least one silicon-containing s-triazine substituted with two aminobenzoate or aminobenzamide groups of formula (I) or one of its tautomeric forms, more fully defined below; and b) at least one non-silicon-containing lipophilic 1,3,5-triazine-type UV-screening agent.

This invention also features the use of at least one silicon-containing s-triazine substituted with two aminobenzoate or aminobenzamide groups of formula (I) or one of its tautomeric forms, formulated into a composition comprising, in a cosmetically acceptable carrier, at least one non-silicon-containing lipophilic 1,3,5-triazine-type UV-screening agent, for improving the photoprotective effectiveness of the composition in the UV-B range.

The present invention also features the formulation of at least one silicon-containing s-triazine substituted with two aminobenzoate or aminobenzamide groups of formula (I) or one of its tautomeric forms, into a composition comprising, in a cosmetically acceptable carrier, at least one non-silicon-containing lipophilic 1,3,5-triazine-type UV-screening agent, for improving the solubility of said non-silicon-containing triazine screening agent in the composition.

Other features, aspects and advantages of the invention will become apparent from the detailed description which follows.

Herein, the expression "UV-radiation-screening system" means a UV-radiation-screening agent containing either a single UV-radiation-screening organic or inorganic compound, or a mixture of several UV-radiation-screening organic or inorganic compounds, for example a mixture comprising a UV-A-screening agent and a UV-B-screening agent.

The term "cosmetically acceptable" means compatible with the skin and/or its integuments, which has a pleasant color, smell and feel, and which does not cause any unacceptable discomfort (stinging, tautness, redness), that may dissuade the consumer from using this composition.

The term "lipophilic screening agent" means any screening agent that can be completely dissolved in the molecular state in a liquid fatty phase or else that can be solubilized in colloidal form (for example, in micellar form) in a liquid fatty phase.

The term "silicon-containing" means a compound which comprises at least one diorganosiloxane group or one silane group in its structure.

The term "non-silicon-containing" means a compound which does not comprise at least one diorganosiloxane group or one silane group in its structure.

DETAILED DESCRIPTION OF BEST MODE AND SPECIFIC/PREFERRED EMBODIMENTS OF THE INVENTION

The silicon-containing s-triazine compounds substituted with two aminobenzoate or aminobenzamide groups in accordance with the invention have the following general formula (I) or one of its tautomeric forms:

in which:

the radicals R, which may be identical or different, are each a linear or branched and optionally halogenated or unsaturated $C_1$-$C_{30}$ alkyl radical, a $C_6$-$C_{12}$ aryl radical, a $C_1$-$C_{10}$ alkoxy radical or the trimethylsilyloxy group;

$\underline{a}$=0 to 3;

the group D is an s-triazine compound of formula (II) below:

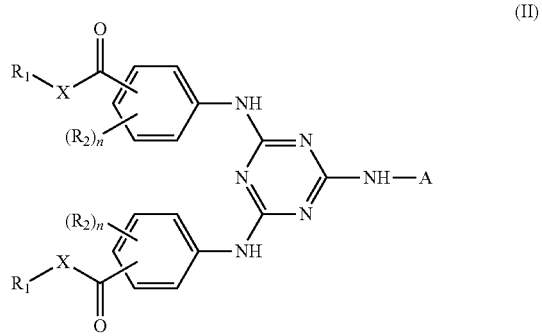

in which:

X is —O— or —$NR_3$—, in which $R_3$ is hydrogen or a $C_1$-$C_5$ alkyl radical, $R_1$ is a linear or branched and optionally unsaturated $C_1$-$C_{20}$ alkyl radical that may contain a silicon atom, a $C_5$-$C_{20}$ cycloalkyl radical optionally substituted with 1 to 3 linear or branched $C_1$-$C_4$ alkyl radicals, the —$(CH_2CHR_4$—$O)_mR_5$ group or the —$CH_2$—$CH(OH)$—$CH_2$—$O$—$R_6$ group, $R_4$ is hydrogen or methyl; it being possible for the (C═O)$XR_1$ group to be in the ortho-, meta- or para-position with respect to the amino group, $R_5$ is hydrogen or a $C_1$-$C_8$ alkyl radical, $R_6$ is hydrogen or a $C_4$-$C_8$ alkyl radical, m is an integer ranging from 2 to 20, n=0 to 2, the radicals $R_2$, which may be identical or different, are each a hydroxyl radical, a linear or branched $C_1$-$C_8$ alkyl radical, or a $C_1$-$C_8$ alkoxy radical, with the proviso that two adjacent $R_2$ radicals of the same aromatic ring may together form an alkylidenedioxy group in which the alkylidene group contains 1 or 2 carbon atoms, A is a divalent radical selected from among methylene, —[CH(Si(CH$_3$)$_3$)]—, ethylene or a group corresponding to one of the following formulae (III), (IV) and (V):

in which:

Z is a linear or branched, saturated or unsaturated $C_1$-$C_{10}$ alkylene diradical optionally substituted with a hydroxyl radical or oxygen and that may optionally contain an amino group, W is a hydrogen atom, a hydroxyl radical or a linear or branched, saturated or unsaturated $C_1$-$C_8$ alkyl radical.

It should be noted that the derivatives of formula (I) can be used in their tautomeric forms, and more particularly in the tautomeric form of formula (I') below:

$$(D')-(Si)-O_{(3-a)/2} \quad (R)_a \quad (I')$$

in which the group D' is an s-triazine compound of formula (II') below:

(II')

[Structure of s-triazine compound with $R_1$, X, $(R_2)_n$, NH, N, NH—A groups]

In addition to the units of formula -A-(Si)(R)$_a$(O)$_{(3-a)/2}$, the organosiloxane can contain structural units of formula $$(R)_b-(Si)(O)_{(4-b)/2}$$

in which:
R has the same definition as in formula (I),
b=1, 2 or 3.

The preferred s-triazine derivatives are those for which, in formula (II) or (II'), at least one, and even more preferably all, of the following conditions are satisfied:
R is methyl,
a=1 or 2,
X is O,
$R_1$ is a $C_4$-$C_5$ radical,
n=0, the (C=O)XR$_1$ group is in the para-position with respect to the amino group,
Z=—CH$_2$—,
W=H.

Preferably, the s-triazine compounds of the invention are represented by the following formulae (Ia), (Ib) or (Ic):

(Ia)
$$(B)-\underset{R_7}{\overset{R_7}{Si}}-O+\underset{R_7}{\overset{R_7}{Si}}-O\underset{r}{\rightarrow}+\underset{(D)}{\overset{R_7}{Si}}-O\underset{s}{\rightarrow}\underset{R_7}{\overset{R_7}{Si}}-(B)$$

(Ib)
$$+O-\underset{R_7}{\overset{R_7}{Si}}\rightarrow_t+O-\underset{(D)}{\overset{R_7}{Si}}\rightarrow_u$$

(Ic)
$$(D)-Si(R_8)_3$$

in which:
(D) corresponds to formula (II) as defined above, the radicals $R_7$, which may be identical or different, are selected from among linear or branched $C_1$-$C_{20}$ alkyl, phenyl, 3,3,3-trifluoropropyl and trimethylsilyloxy radicals or the hydroxyl radical, the radicals $R_8$, which may be identical or different, are selected from among linear or branched $C_1$-$C_{20}$ alkyl and alkenyl radicals, the hydroxyl radical or the phenyl radical, the radicals (B), which may be identical or different, are selected from among the radicals $R_7$ and the radical (D), r is an integer ranging from 0 to 200 inclusive, s is an integer ranging from 0 to 50, and if s=0, at least one of the two symbols (B) is (D), u is an integer ranging from 1 to 10, t is an integer ranging from 0 to 10, with the proviso that t+u is greater than or equal to 3, and also their tautomeric forms.

The linear diorganosiloxanes of formula (Ia) are particularly preferred.

The linear or cyclic diorganosiloxanes of formula (Ia) or (Ib) according to the present invention are random polymers or oligomers preferably having at least one, and even more preferably all, of the following characteristics:

$R_7$ is the methyl radical or the hydroxyl radical,

B is preferably methyl (in the case of the linear compounds of formula (Ia)).

By way of examples of particularly preferred compounds of formula (I), representative are the compounds of formulae (a) to (m) below, and also their tautomeric forms:

(a)

[Chemical structure (a)]

(b)

[Chemical structure (b)]

-continued
(c)
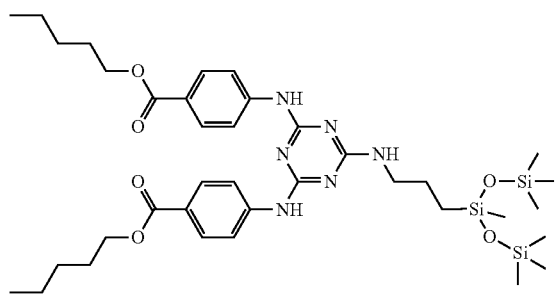
(d)
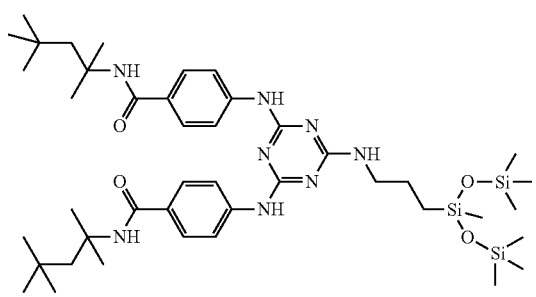
(e)
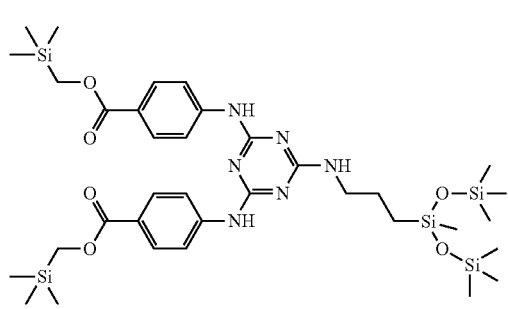
(f)
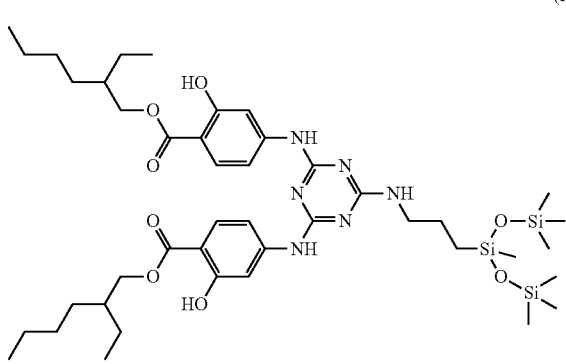
(g)
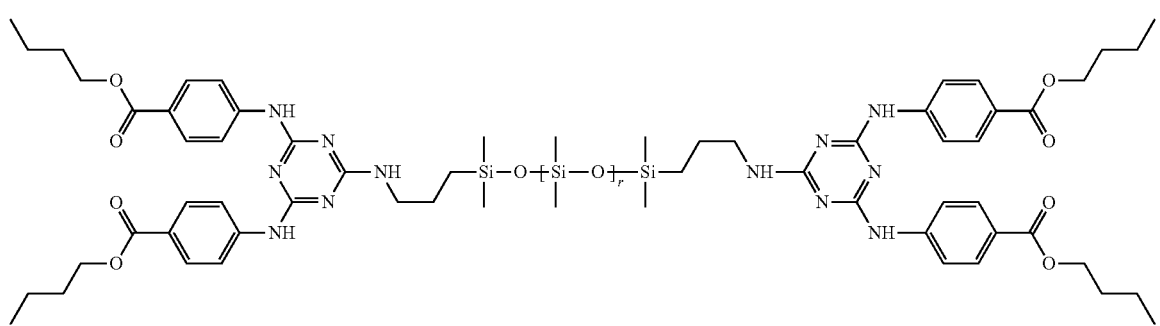
(h)
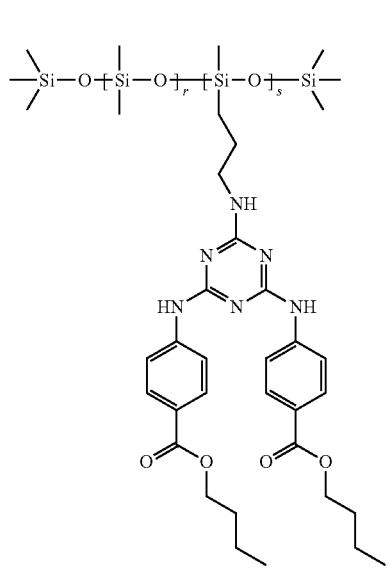
(i)
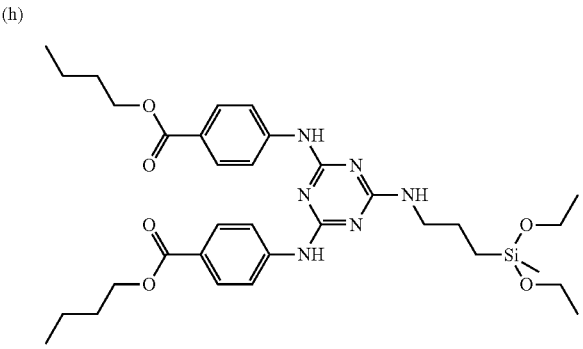

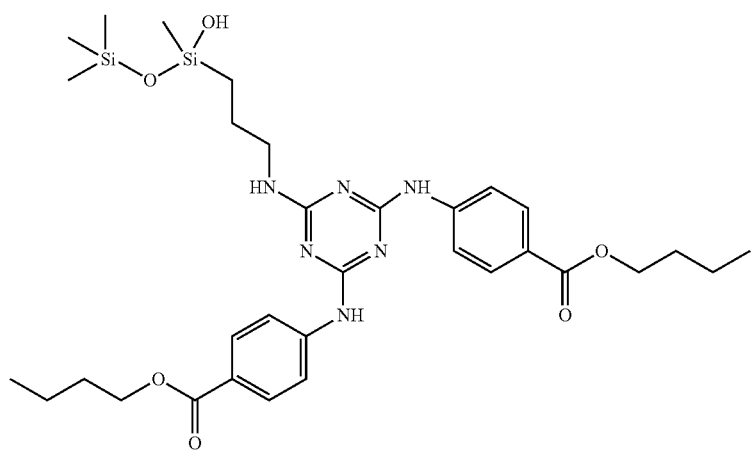
(j)
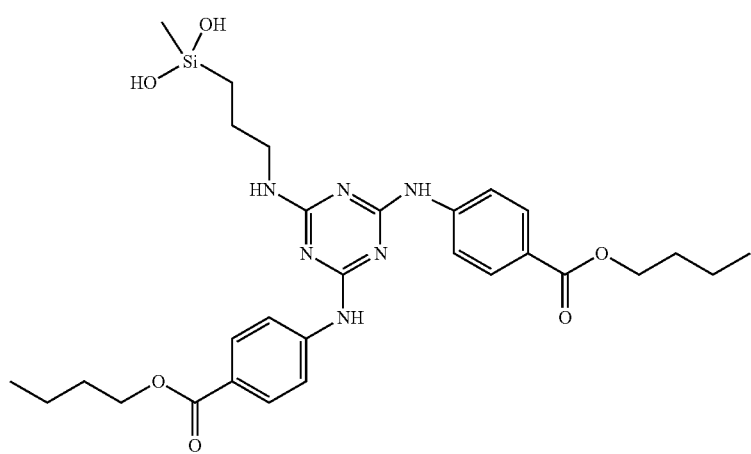
(k)
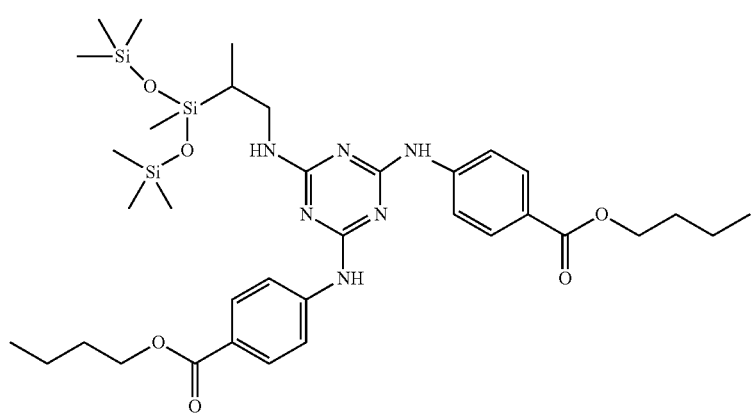
(l)

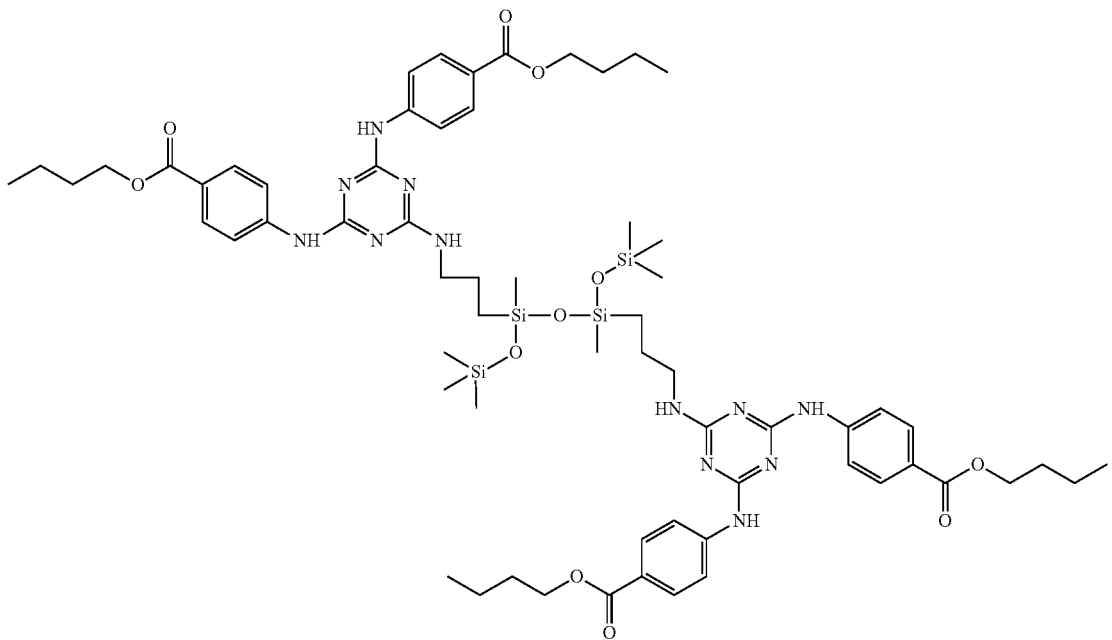

(m)

More particularly preferred is the compound 2,4-bis(n-butyl 4'-diylaminobenzoate)-6-{[1,3,3,3-tetramethyl-1-[(trimethylsilyl)oxy]disiloxanyl]propyl-3-ylamino}-s-triazine of structure (b):

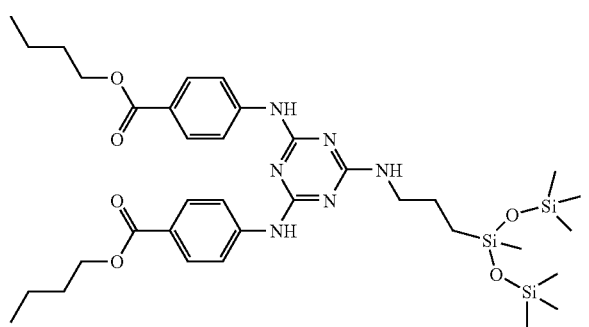

(b)

The compounds of formula (I) can be prepared according to the reaction scheme below:

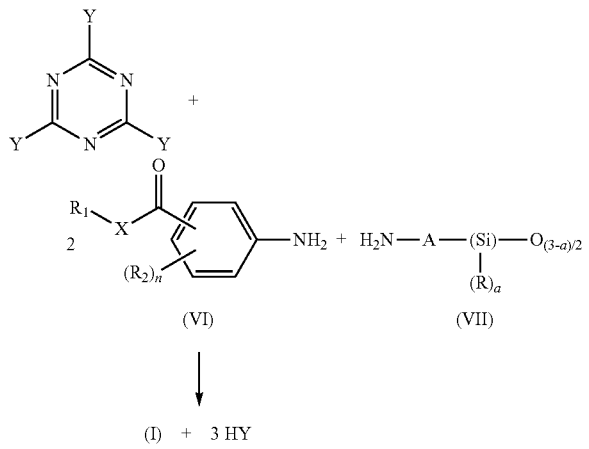

in which R, $R_1$, $R_2$, A, n and $a$ correspond to the definitions above and Y is a halogen, in particular chlorine or bromine.

The reactants can be introduced in any order; 2 equivalents of the derivative of formula (VI) followed by 1 equivalent of the derivative of formula (VII) (pathway 1) or 1 equivalent of the derivative of formula (VII) followed by 2 equivalents of the derivative of formula (VI) (pathway 2).

The above reactions can be carried out optionally in the presence of a solvent (for example: THF, acetone/water for the first stage: toluene, xylene or 1,2-dichloroethane for the second stage), at a temperature of from 0° C. and 200° C., more particularly from 0° C. and 20° C. for the first stage, and from 50° C. and 120° C. for the second stage, and in the presence or absence of a base which captures the acid formed (for example: sodium bicarbonate, sodium carbonate, aqueous sodium hydroxide, triethylamine or pyridine). They can also be carried out in microwaves in the presence or absence of a solvent (for example: toluene, xylene or 1,2-dichloroethane) or in the presence or absence of 10% of graphite, at a temperature of 50 to 150° C., at a power of 50-150 watts for a period of 10 to 30 minutes.

When $a$ is equal to 1-3 and R is an alkoxy, the polymerizations of the alkoxysilane monomer derivatives can be carried out by conventional silicone chemistry methods.

The preparation of the aminated derivatives of benzoic acid of formula (VI) is described in particular in FR-2,151,503. As aminated derivatives of benzoic acid that are particularly suitable for the preparation of the compounds according to the invention, exemplary are butyl 4-aminobenzoate and pentyl 4-aminobenzoate.

The aminated silicones of formula (VII) can be obtained from Dow Corning Toray Silicone Co. Ltd, such as those with α,ω-diamino structure, for instance BY16-853 (viscosity: 30; $NH_2$ equivalent: 650) or BY16-853B (viscosity: 80; $NH_2$ equivalent: 2200), or those with a pendent group structure, for instance BY16-828 (viscosity: 120; $NH_2$ equivalent: 3500) or BY16-850 (viscosity: 1100; $NH_2$ equivalent: 4000); the aminomethyltrimethylsilane marketed by Gelest and bis(trimethylsilyl)methylamine (RN 134340-00-4).

The s-triazine compounds of formula (I) in accordance with the invention are preferably present in the subject compositions at contents ranging from 0.01% to 20% by weight, and more preferably from 0.1% to 10%, and even more preferably from 0.1% to 6% by weight, relative to the total weight of the composition.

The non-silicon-containing lipophilic 1,3,5-triazine-type UV-screening agents can in particular be selected from among the 1,3,5-triazine derivatives of formula (VIII) below:

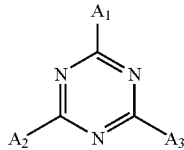

(VIII)

in which the radicals $A_1$, $A_2$ and $A_3$, which may be identical or different, are selected from among the groups of formula (IX):

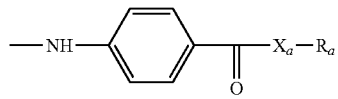

(IX)

in which:

$X_a$, which may be identical or different, represent oxygen or the —NH-radical;

the radicals $R_a$, which may be identical or different, are selected from among hydrogen; an alkali metal; an ammonium radical optionally substituted with one or more alkyl or hydroxyalkyl radicals; a linear or branched $C_1$-$C_{18}$ alkyl radical; a $C_5$-$C_{12}$ cycloalkyl radical optionally substituted with one or more $C_1$-$C_4$ alkyl radicals; a polyoxyethylenated radical comprising from 1 to 6 ethylene oxide units and the terminal OH group of which is methylated; a radical of formula (X), (XI) or (XII) below:

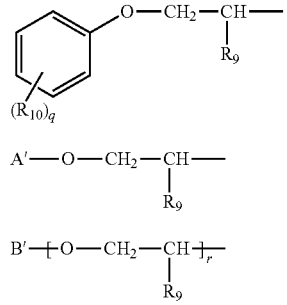

(X)

(XI)

(XII)

in which:

$R_9$ is hydrogen or a methyl radical;
$R_{10}$ is a $C_1$-$C_8$ alkyl radical;
q is an integer ranging from 0 to 3;
r is an integer ranging from 1 to 10;
A' is a $C_4$-$C_8$ alkyl radical or a $C_5$-$C_8$ cycloalkyl radical;
B' is selected from among a linear or branched $C_1$-$C_8$ alkyl radical; a $C_5$-$C_8$ cycloalkyl radical; an aryl radical optionally substituted with one or more $C_1$-$C_4$ alkyl radicals.

A first more particularly preferred family of 1,3,5-triazine derivatives, in particular described in EP-A-0,517,104, is that of the 1,3,5-triazines corresponding to formula (VIII) in which $A_1$, $A_2$ and $A_3$ are of formula (IX) and have the following characteristics:

one of the $X_a$—$R_a$ radicals is the —NH—$R_a$ radical with $R_a$ selected from among a $C_5$-$C_{12}$ cycloalkyl radical optionally substituted with one or more $C_1$-$C_4$ alkyl radicals; a radical of formula (X), (XI) or (XII) above in which B' is a $C_1$-$C_4$ alkyl radical and $R_{10}$ is the methyl radical;

the other two $X_a$—$R_a$ represent the —O—$R_a$ radical with $R_a$, which may be identical or different, selected from among hydrogen; an alkali metal; an ammonium radical optionally substituted with one or more alkyl or hydroxyalkyl radicals; a linear or branched $C_1$-$C_{18}$ alkyl radical; a $C_5$-$C_{12}$ cycloalkyl radical optionally substituted with one or more $C_1$-$C_4$ alkyl radicals; a radical of formula (X), (XI) or (XII) above in which B' is a $C_1$-$C_4$ alkyl radical and $R_{10}$ is the methyl radical.

A second more particularly preferred family of 1,3,5-triazine derivatives, in particular described in EP-A-0,570,838, is that of the 1,3,5-triazines corresponding to formula (VIII) in which $A_1$, $A_2$ and $A_3$ are of formula (IX) and have all the following characteristics:

one or two $X_a$—$R_a$ represent(s) the —NH—$R_a$ radical, with $R_a$ selected from among a linear or branched $C_1$-$C_{18}$ alkyl radical; a $C_5$-$C_{12}$ cycloalkyl radical optionally substituted with one or more $C_1$-$C_4$ alkyl radicals; a radical of formula (X), (XI) or (XII) above in which B' is a $C_1$-$C_4$ alkyl radical and $R_{10}$ is the methyl radical;

the other or other two $X_a$—$R_a$ being the —O—$R_a$ radical with $R_a$, which may be identical or different, selected from among hydrogen; an alkali metal; an ammonium radical optionally substituted with one or more alkyl or hydroxyalkyl radicals; a linear or branched $C_1$-$C_{18}$ alkyl radical; a $C_5$-$C_{12}$ cycloalkyl radical optionally substituted with one or more $C_1$-$C_4$ alkyl radicals; a radical of formula (X), (XI) or (XII) above in which: B' is a $C_1$-$C_4$ alkyl radical and $R_{10}$ is the methyl radical.

A particularly preferred 1,3,5-triazine of this second family is 2-[(p-(tert-butylamido)anilino]-4,6-bis[(p-(2'-ethylhexyl-1'-oxycarbonyl)anilino]-1,3,5-triazine or "Diethylhexyl Butamido Triazone" marketed under the trademark "Uvasorb HEB" by Sigma 3V and corresponding to the following formula:

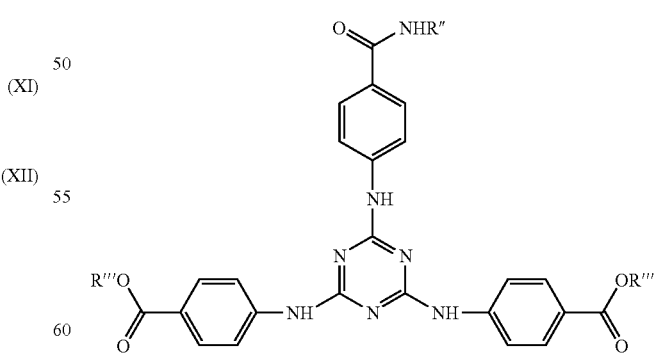

in which R'" is a 2-ethylhexyl radical and R" is a tert-butyl radical.

A third preferred family of the compounds according to the present invention, and that is in particular described in U.S. Pat. No. 4,724,137, is that of the 1,3,5-triazines corresponding to formula (VIII) in which $A_1$, $A_2$ and $A_3$ are of formula (IX) and have the following characteristics:

$X_a$ are identical and represent oxygen;

the radicals $R_a$, which may be identical or different, are each a $C_6$-$C_{12}$ alkyl radical or a polyoxyethylenated radical having from 1 to 6 ethylene oxide units and the terminal OH group of which is methylated.

A particularly preferred 1,3,5-triazine of this third family is 2,4,6-tris[p-(2'-ethylhexyl-1'-oxycarbonyl)anilino]-1,3,5-triazine or "Ethylhexyl Triazone" marketed in particular under the trademark "Uvinul T 150" by BASF, and corresponds to the following formula:

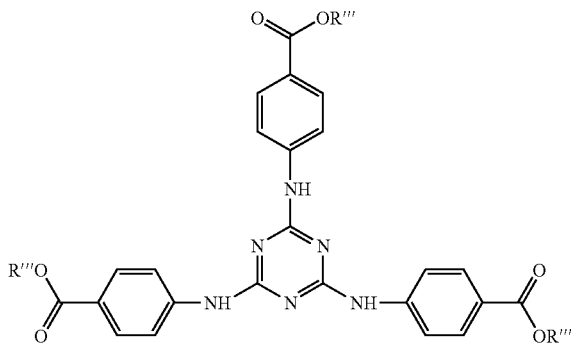

in which R''' is a 2-ethylhexyl radical.

According to a particularly preferred embodiment of the invention, the lipophilic triazine-type UV-screening agents will be selected from among bisresorcinyl triazine compounds, and more particularly from the compounds corresponding to formula (XIII) below:

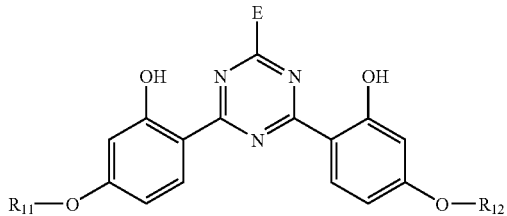

(XIII)

in which:

$R_{11}$ and $R_{12}$, which may be identical or different, are each a linear or branched $C_1$-$C_{30}$ alkyl radical or a linear or branched $C_2$-$C_{30}$ alkenyl radical, E is the radical of formula (IX) or (X) below:

(XIV)

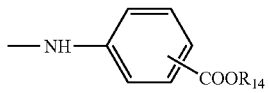

(XV)

in which:

$R_{13}$ is hydrogen, a $C_1$-$C_{20}$ alkyl radical, the —(CH$_2$CHR$_{15}$—O)p-R$_{12}$ radical or the radical of formula —CH$_2$—CH(OH)—CH$_2$—O-T$_1$, $R_{14}$ is hydrogen, a $C_1$-$C_{20}$ alkyl radical or a radical of formula —(CH$_2$)p-O-T$_1$, $R_{15}$ is hydrogen or methyl, $T_1$ is hydrogen or a $C_1$-$C_8$ alkyl radical, o=1-16, p=1-4.

In formulae (XIII), (XIV) and/or (XV) described above:

the alkyl radicals are linear or branched and are selected, for example, from among methyl, ethyl, n-propyl, isopropyl, n-butyl, sec-butyl, tert-butyl, amyl, isoamyl, tert-amyl, heptyl, octyl, isooctyl, nonyl, decyl, undecyl, dodecyl, tetradecyl, pentadecyl, hexadecyl, heptadecyl or octadecyl radicals;

the alkenyl radicals are selected, for example, from among allyl, methallyl, isopropenyl, 2-butenyl, 3-butenyl, isobutenyl, n-penta-2,4-dienyl, 3-methylbut-2-enyl, 2-n-octenyl, 2-n-dodecenyl, isododecenyl or 4-n-octadecenyl radicals.

The bisresorcinyl triazine derivatives of formula (XIII) of the invention are screening agents that are already known per se. They are described and prepared according to the syntheses indicated in EP-A-0,775.698.

By way of examples of compounds of formula (VIII) that can be used, representative are:

2,4-bis{[4-(2-ethylhexyloxy)-2-hydroxy]phenyl}-6-(4-methoxyphenyl)-1,3,5-triazine;

2,4-bis{[4-(3-(2-propyloxy)-2-hydroxypropyloxy)-2-hydroxy]phenyl}-6-(4-methoxyphenyl)-1,3,5-triazine;

2,4-bis{[4-(2-ethylhexyloxy)-2-hydroxy]phenyl}-6-[4-(2-methoxyethylcarboxyl)phenylamino]-1,3,5-triazine;

2,4-bis{[4-(2"-methylpropenyloxy)-2-hydroxy]phenyl}-6-(4-methoxyphenyl)-1,3,5-triazine;

2,4-bis{[4-(3-(2-propyloxy)-2-hydroxypropyloxy]-2-hydroxy]phenyl}-6-[(4-ethylcarboxyl)phenylamino]-1,3,5-triazine;

2,4-bis{[4-(2-ethylhexyloxy)-2-hydroxy]phenyl}-6-(1-methylpyrrol-2-yl)-1,3,5-triazine.

The compound derived from bisresorcinol triazine that is more particularly preferred according to the invention will be the compound 2,4-bis{[4-(2-ethylhexyloxy)-2-hydroxy]phenyl}-6-(4-methoxyphenyl)-1,3,5-triazine (INCI name: "Bis-Ethylhexyloxyphenol Methoxyphenyl Triazine" marketed under the trademark "Tinosorb S" by Ciba Geigy.

The non-silicon-containing lipophilic 1,3,5-triazine compounds are preferably present in the compositions in accordance with the invention at contents ranging from 0.01% to 20% by weight, and more preferably from 0.1% to 10%, and even more preferably from 0.1% to 6% by weight, relative to the total weight of the composition.

The compositions according to the invention are generally suitable for topical application to the skin and therefore generally comprise a physiologically acceptable medium, i.e., a medium which is compatible with the skin and/or its integuments (hair, eyelashes, eyebrows, lips, nails). It is preferably a cosmetically acceptable medium, i.e., a medium which has a pleasant color, smell and feel and which does not cause any unacceptable discomfort (stinging, tautness, redness) liable to dissuade the consumer from using this composition.

The compositions in accordance with the invention can also contain other supplementary organic or inorganic UV-screening agents that are active in the UV-A range and/or UV-B range.

Of course, one skilled in the art will take care to select the optional supplementary screening agents and/or the amounts thereof in such a manner that the advantageous properties intrinsically associated with the compositions in accordance with the invention are not, or not substantially, impaired by the envisaged addition(s).

The supplementary organic photoprotective agents are in particular selected from among the anthranilates; cinnamic derivatives; salicylic derivatives, camphor derivatives; benzophenone derivatives; β,β-diphenyl acrylate derivatives; benzalmalonate derivatives; benzimidazole derivatives; imidazolines; bisbenzoazolyl derivatives as described in EP-669,323 and U.S. Pat. No. 2,463,264; p-aminobenzoic acid (PABA) derivatives; benzoxazole derivatives as described in EP-0,832,642, EP-1,027,883, EP-1,300,137 and DE-10162844; screening polymers and screening silicones such as those described in particular in application WO-93/04665; dimers derived from α-alkylstyrene, such as those described in DE-19855649; 4,4-diarylbutadienes as described in applications EP-0,967,200, DE-19746654, DE-19755649, EP-A-1,008,586, EP-1,133,980 and EP-133,981, and mixtures thereof.

The supplementary organic photoprotective agents can also be selected from among dibenzoylmethane derivatives.

As examples of supplementary organic photoprotective agents, representative are those noted below under their INCI name:

para-Aminobenzoic Acid Derivatives:
PABA,
Ethyl PABA,
Ethyl Dihydroxypropyl PABA,
Ethylhexyl Dimethyl PABA marketed in particular under the trademark "Escalol 507" by ISP,
Glyceryl PABA,
PEG-25 PABA marketed under the trademark "Uvinol P25" by BASF, Dibenzoylmethane Derivatives:
Butyl Methoxydibenzoylmethane marketed in particular under the trademark "Parsol 1789" by Roche Vitamins,
Isopropyl Dibenzoylmethane marketed under the trademark "Eusolex 8020" by Merck, Salicylic Derivatives:
Homosalate, marketed under the trademark "Eusolex HMS" by Rona/EM Industries,
Ethylhexyl Salicylate, marketed under the trademark "Neo Heliopan OS" by Haarmann and Reimer,
Dipropyleneglycol Salicylate, marketed under the trademark "Dipsal" by Scher,
TEA Salicylate, marketed under the trademark "Neo Heliopan TS" by Haarmann and Reimer, Cinnamic Derivatives:
Ethylhexyl Methoxycinnamate, marketed in particular under the trademark "Parsol MCX" by Hoffmann-LaRoche,
Isopropyl Methoxycinnamate,
Isoamyl Methoxycinnamate, marketed under the trademark "Neo Heliopan E 1000" by Haarmann and Reimer,
Cinoxate,
DEA Methoxycinnamate,
Diisopropyl Methylcinnamate,
Glyceryl Ethylhexanoate Dimethoxycinnamate, β,β-Diphenylacrylate Derivatives:
Octocrylene, marketed in particular under the trademark "Uvinul N539" by BASF,
Etocrylene, marketed in particular under the trademark "Uvinul N35" by BASF, Benzophenone Derivatives:
Benzophenone-1, marketed under the trademark "Uvinul 400" by BASF,
Benzophenone-2, marketed under the trademark "Uvinul D50" by BASF,
Benzophenone-3 or Oxybenzone, marketed under the trademark "Uvinul M40" by BASF,
Benzophenone-4, marketed under the trademark "Uvinul MS40" by BASF,
Benzophenone-5,
Benzophenone-6, marketed under the trademark "Helisorb 11" by Norquay,
Benzophenone-8, marketed under the trademark "Spectra-Sorb UV-24" by American Cyanamid,
Benzophenone-9, marketed under the trademark "Uvinul DS-49" by BASF,
Benzophenone-12, Benzylidenecamphor Derivatives:
3-Benzylidene camphor, manufactured under the trademark "Mexoryl SD" by Chimex,
4-Methylbenzylidene camphor, marketed under the trademark "Eusolex 6300" by Merck,
Benzylidene Camphor Sulfonic Acid, manufactured under the trademark "Mexoryl SL" by Chimex,
Camphor Benzalkonium Methosulfate, manufactured under the trademark "Mexoryl SO" by Chimex,
Terephthalylidene Dicamphor Sulfonic Acid, manufactured under the trademark "Mexoryl SX" by Chimex,
Polyacrylamidomethyl Benzylidene Camphor, manufactured under the trademark "Mexoryl SW" by Chimex, Phenylbenzimidazole Derivatives:
Phenylbenzimidazole Sulfonic Acid, marketed in particular under the trademark "Eusolex 232" by Merck,
Disodium Phenyl Dibenzimidazole Tetrasulfonate, marketed under the trademark "Neo Heliopan AP" by Haarmann and Reimer, Anthranilic Derivatives:
Methyl anthranilate, marketed under the trademark "Neo Heliopan MA" by Haarman and Reimer, Imidazoline Derivatives:
Ethylhexyl Dimethoxybenzylidene Dioxoimidazoline Propionate, Benzalmalonate Derivatives:
Polyorganosiloxane comprising benzalmalonate functional groups, such as Polysilicone-15, marketed under the trademark "Parsol SLX" by Hoffmann La Roche, 4,4-Diarylbutadiene Derivatives:
1,1-dicarboxy-(2,2'-dimethylpropyl)-4,4-diphenylbutadiene.

The preferred supplementary organic photoprotective agents are selected from among:
Ethylhexyl Methoxycinnamate,
Homosalate,
Ethylhexyl Salicylate,
Octocrylene,
Phenylbenzimidazole Sulfonic Acid,
Terephthalylidene Dicamphor Sulfonic Acid
Benzophenone-3,
Benzophenone-4,
Benzophenone-5,
4-Methylbenzylidenecamphor,
Disodium Phenyl Dibenzimidazole Tetrasulfonate,
Polysilicone-15,
1,1-Dicarboxy-(2,2'-dimethylpropyl)-4,4-diphenylbutadiene,
and mixtures thereof.

The supplementary inorganic photoprotective agents are selected from among pigments formed from metal oxides which may or may not be coated (average size of the primary particles: generally from 5 nm and 100 nm, preferably from 10 nm and 50 nm), such as, for example, pigments formed from titanium oxide (amorphous or crystalline in the rutile and/or anatase form), iron oxide, zinc oxide, zirconium oxide or cerium oxide, which are all UV photoprotective agents well known per se.

The pigments may be coated or uncoated.

The coated pigments are pigments which have been subjected to one or more surface treatments of chemical, electronic, mechanochemical and/or mechanical nature with compounds such as described, for example, in *Cosmetics & Toiletries*, February 1990, Vol. 105, pp. 53-64, such as amino acids, beeswax, fatty acids, fatty alcohols, anionic surfactants, lecithins, sodium, potassium, zinc, iron or aluminum salts of fatty acids, metal alkoxides (titanium or aluminum alkoxides), polyethylene, silicones, proteins (collagen, elastin), alkanolamines, silicon oxides, metal oxides or sodium hexametaphosphate.

In known manner, the silicones are organosilicon polymers or oligomers comprising a linear or cyclic and branched or crosslinked structure, of variable molecular weight, obtained by polymerization and/or polycondensation of suitable functional silanes and essentially composed of a repetition of main units in which the silicon atoms are connected to one another via oxygen atoms (siloxane bond), optionally substituted hydrocarbon radicals being connected directly to the said silicon atoms via a carbon atom.

The term "silicones" also encompasses the silanes necessary for their preparation, in particular alkylsilanes.

The silicones used for the coating of the pigments suitable for the present invention are preferably selected from the group consisting of alkylsilanes, polydialkylsiloxanes and polyalkylhydrosiloxanes. More preferably still, the silicones are selected from the group consisting of octyltrimethylsilane, polydimethylsiloxanes and polymethylhydrosiloxanes.

Of course, the pigments formed of metal oxides may, before their treatment with silicones, have been treated with other surfacing agents, in particular with cerium oxide, alumina, silica, aluminum compounds, silicon compounds or their mixtures.

The coated pigments are more particularly titanium oxides coated:
with silica, such as the product "Sunveil" from Ikeda and the product "Eusolex T-AVO" from Merck;
with silica and with iron oxide, such as the product "Sunveil F" from Ikeda;
with silica and with alumina, such as the products "Microtitanium Dioxide MT 500 SA" and "Microtitanium Dioxide MT 100 SA" from Tayca, "Tioveil" from Tioxide and "Mirasun TiW 60" from Rhodia;
with alumina, such as the products "Tipaque TTO-55 (B)" and "Tipaque TTO-55 (A)" from Ishihara and "UVT 14/4" from Kemira;
with alumina and with aluminum stearate, such as the product "Microtitanium Dioxide MT 100 TV, MT 100 TX, MT 100 Z or MT-01 from Tayca and the products "Solaveil CT-10 W", "Solaveil CT 100" and "Solaveil CT 200" from Uniqema;
with silica, with alumina and with alginic acid, such as the product "MT-100 AQ" from Tayca;
with alumina and with aluminum laurate, such as the product "Microtitanium Dioxide MT 100 S" from Tayca;
with iron oxide and with iron stearate, such as the product "Microtitanium Dioxide MT 100 F" from Tayca;
with zinc oxide and with zinc stearate, such as the product "BR351" from Tayca;
with silica and with alumina and treated with a silicone, such as the products "Microtitanium Dioxide MT 600 SAS", "Microtitanium Dioxide MT 500 SAS" or "Microtitanium Dioxide MT 100 SAS" from Tayca;
with silica, with alumina and with aluminum stearate and treated with a silicone, such as the product "STT-30-DS" from Titan Kogyo;
with silica and treated with a silicone, such as the product "UV-Titan X 195" from Kemira or the product SMT-100 WRS from Tayca;
with alumina and treated with a silicone, such as the products "Tipaque TTO-55 (S)" from Ishihara or "UV Titan M 262" from Kemira; with triethanolamine, such as the product "STT-65-S" from Titan Kogyo;
with stearic acid, such as the product "Tipaque TTO-55 (C)" from Ishihara;
with sodium hexametaphosphate, such as the product "Microtitanium Dioxide MT 150 W" from Tayca.

Other titanium oxide pigments treated with a silicone are preferably $TiO_2$ treated with octyltrimethylsilane and for which the mean size of the individual particles is from 25 and 40 nm, such as that marketed under the trademark "T 805" by Degussa Silices, $TiO_2$ treated with a polydimethylsiloxane and for which the mean size of the individual particles is 21 nm, such as that marketed under the trademark "70250 Cardre UF $TiO_2SI3$" by Cardre, anatase/rutile $TiO_2$ treated with a polydimethylhydrosiloxane and for which the mean size of the individual particles is 25 nm, such as that marketed under the trademark "Microtitanium Dioxyde USP Grade Hydrophobic" by Color Techniques.

The uncoated titanium oxide pigments are, for example, marketed by Tayca under the trademarks "Microtitanium Dioxide MT 500 B" or "Microtitanium Dioxide MT600 B", by Degussa under the trademark "P 25", by Wacker under the trademark "Oxyde de titane transparent PW", by Miyoshi Kasei under the trademark "UFTR", by Tomen under the trademark "ITS" and by Tioxide under the trademark "Tioveil AQ".

The uncoated zinc oxide pigments are, for example:
those marketed under the trademark "Z-cote" by Sunsmart;
those marketed under the trademark "Nanox" by Elementis;
those marketed under the trademark "Nanogard WCD 2025" by Nanophase Technologies.

The coated zinc oxide pigments are, for example:
those marketed under the trademark "Z-cote HP1" by Sunsmart (ZnO coated with dimethicone);
those marketed under the trademark "Oxide zinc CS-5" by Toshibi (ZnO coated with polymethylhydrosiloxane);
those marketed under the trademark "Nanogard Zinc Oxide FN" by Nanophase Technologies (as a 40% dispersion in Finsolv TN, $C_{12}$-$C_{15}$ alkyl benzoate);
those marketed under the trademark "Daitopersion Zn-30" and "Daitopersion Zn-50" by Daito (dispersions in oxyethylenated polydimethylsiloxane/cyclopolymethylsiloxane comprising 30% or 50% of zinc nanooxides coated with silica and polymethylhydrosiloxane);
those marketed under the trademark "NFD Ultrafine ZnO" by Daikin (ZnO coated with phosphate of perfluoroalkyl and copolymer based on perfluoroalkylethyl as a dispersion in cyclopentasiloxane);
those marketed under the trademark "SPD-Z1" by Shin-Etsu (ZnO coated with silicone-grafted acrylic polymer dispersed in cyclodimethylsiloxane);
those marketed under the trademark "Escalol Z100" by ISP (alumina-treated ZnO dispersed in the ethylhexyl methoxycinnamate/PVP-hexadecene copolymer/methicone mixture);
those marketed under the trademark "Fuji ZnO-SMS-10" by Fuji Pigment (ZnO coated with silica and polymethylsilsesquioxane);

those marketed under the trademark "Nanox Gel TN" by Elementis (ZnO dispersed at 55% in $C_{12}$-$C_{15}$ alkyl benzoate with hydroxystearic acid polycondensate).

The uncoated cerium oxide pigments are marketed, for example, under the trademark "Colloidal Cerium Oxide" by Rhône-Poulenc.

The uncoated iron oxide nanopigments are, for example, marketed by Arnaud under the trademarks "Nanogard WCD 2002 (FE 45B)", "Nanogard Iron FE 45 BL AQ", "Nanogard FE 45R AQ" or "Nanogard WCD 2006 (FE 45R)", or by Mitsubishi under the trademark "TY-220".

The coated iron oxide pigments are, for example, marketed by Arnaud under the trademarks "Nanogard WCD 2008 (FE 45B FN)", "Nanogard WCD 2009 (FE 45B 556)", "Nanogard FE 45 BL 345" or "Nanogard FE 45 BL" or by BASF under the trademark "Oxyde de fer transparent".

Also exemplary are mixtures of metal oxides, in particular of titanium dioxide and of cerium dioxide, including the mixture of equal weights of titanium dioxide coated with silica and of cerium dioxide coated with silica marketed by Ikeda under the trademark "Sunveil A", and also the mixture of titanium dioxide and of zinc dioxide coated with alumina, with silica and with silicone, such as the product "M 261" marketed by Kemira, or coated with alumina, with silica and with glycerol, such as the product "M 211" marketed by Kemira.

The additional photoprotective agents are generally present in the compositions according to the invention in proportions ranging from 0.01 to 20% by weight, with respect to the total weight of the composition, and preferably ranging from 0.1 to 10% by weight, with respect to the total weight of the composition.

The compositions according to the invention can also comprise agents for the artificial tanning and/or browning of the skin (self-tanning agents) and more particularly dihydroxyacetone (DHA). They are preferably present in amounts ranging from 0.1 to 10% by weight, with respect to the total weight of the composition.

The aqueous compositions in accordance with the present invention can additionally comprise conventional cosmetic adjuvants selected in particular from among fatty substances, organic solvents, ionic or nonionic and hydrophilic or lipophilic thickeners, demulcents, humectants, opacifiers, stabilizers, emollients, silicones, anti-foams, fragrances, preservatives, anionic, cationic, nonionic, zwitterionic or amphoteric surfactants, active agents, fillers, polymers, propellants, basifying agents or acidifying agents or any other ingredient commonly used in the cosmetics and/or dermatological field.

The fatty substances can be an oil or a wax, other than the non-polar waxes as defined above, or their mixtures. The term "oil" means a compound which is liquid at ambient temperature. The term "wax" means a compound which is solid or substantially solid at ambient temperature and which has a melting point generally of greater than 35° C.

Exemplary oils are mineral oils (liquid paraffin); plant oils (sweet almond oil, macadamia oil, blackcurrant seed oil or jojoba oil); synthetic oils, such as perhydrosqualene, fatty alcohols, fatty acids or fatty esters, such as the $C_{12}$-$C_{15}$ alkyl benzoates marketed under the trademark "Finsolv TN" or "Witconol TN" by Witco, octyl palmitate, isopropyl lanolate, triglycerides, including those of capric/caprylic acids, or dicaprylyl carbonate, marketed under the trademark "Cetiol CC" by Cognis), or oxyethylenated or oxypropylenated fatty esters and ethers; silicone oils (cyclomethicone, polydimethylsiloxanes or PDMSs); fluorinated oils; or polyalkylenes.

Exemplary waxy compounds are of carnauba wax, beeswax, hydrogenated castor oil, polyethylene waxes and polymethylene waxes, such as that marketed under the trademark Cirebelle 303 by Sasol.

Exemplary organic solvents are lower alcohols and polyols. The latter can be selected from among glycols and glycol ethers, such as ethylene glycol, propylene glycol, butylene glycol, dipropylene glycol or diethylene glycol.

Exemplary hydrophilic thickeners are carboxyvinyl polymers, such as the Carbopols (Carbomers) and the Pemulens (acrylate/$C_{10}$-$C_{30}$-alkyl acrylate copolymer); polyacrylamides, such as, for example, the crosslinked copolymers marketed under the trademarks Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) by Seppic; optionally crosslinked and/or neutralized polymers and copolymers of 2-acrylamido-2-methylpropanesulfonic acid, such as the poly(2-acrylamido-2-methylpropanesulfonic acid) marketed by Hoechst under the trademark "Hostacerin AMPS" (CTFA name: ammonium polyacryloyldimethyl taurate) or Simulgel 800, marketed by Seppic (CTFA name: sodium polyacryloyldimethyl taurate/polysorbate 80/sorbitan oleate); copolymers of 2-acrylamido-2-methylpropanesulfonic acid and of hydroxyethyl acrylate, such as Simulgel NS and Sepinov EMT 10, marketed by Seppic; cellulose derivatives, such as hydroxyethylcellulose; polysaccharides and in particular gums, such as xanthan gum; and their mixtures.

Exemplary lipophilic thickeners are synthetic polymers, such as the poly($C_{10}$-$C_{30}$ alkyl acrylates) marketed under the trademarks "Intelimer IPA 13-1" and "Intelimer IPA 13-6" by Landec, or of modified clays, such as hectorite and its derivatives, such as the products marketed under the Bentone names.

Exemplary such active principles include:
vitamins (A, C, E, K, PP, and the like) and their derivatives or precursors, alone or as mixtures;
agents for combating pollution and/or agents for combating free radicals;
depigmenting agents and/or propigmenting agents;
anti-glycation agents;
soothing agents;
NO-synthase inhibitors;
agents which stimulate the synthesis of dermal or epidermal macromolecules and/or which prevent their decomposition;
agents which stimulate the proliferation of fibroblasts;
agents which stimulate the proliferation of keratinocytes;
muscle-relaxing agents;
tightening agents;
mattifying agents;
keratolytic agents;
desquamating agents;
moisturizing agents;
anti-inflammatory agents;
agents which act on the energy metabolism of the cells;
insect repellents;
substance P or substance CRGP antagonists;
agents for combating hair loss and/or for the regrowth of the hair;
anti-wrinkle agents.

Of course, one skilled in the art will take care to select the additional optional compound(s) mentioned above and/or the amounts thereof in such manner that the advantageous properties intrinsically associated with the composition in accordance with the invention are not, or not substantially, impaired by the envisaged addition(s).

The compositions according to the invention can be formulated according to the techniques well known to those skilled in the art. They can in particular be in the form of a simple or complex (O/W, W/O, O/W/O or W/O/W) emulsion, such as a cream or a milk, or of a cream gel; in the form of an aqueous gel; in the form of a lotion. They can optionally be packaged in an aerosol and be in the form of a foam or a spray.

Preferably, the compositions according to the invention are in the form of an oil-in-water or water-in-oil emulsion.

The emulsions generally contain at least one emulsifier selected from among amphoteric, anionic, cationic or nonionic emulsifiers, used alone or as a mixture. The emulsifiers are appropriately selected according to the emulsion to be obtained (W/O or O/w emulsion). The emulsions can also contain other types of stabilizers such as gelling or thickening polymers.

Mention may be made, as emulsifying surfactants which can be used for the preparation of the W/O emulsions, for example, of sorbitan, glycerol or sugar alkyl esters or ethers; silicone surfactants, such as dimethicone copolyols, for example the mixture of cyclomethicone and of dimethicone copolyol marketed under the trademark "DC 5225 C" by Dow Corning, and alkyl dimethicone copolyols, such as lauryl methicone copolyol, marketed under the trademark "Dow Corning 5200 Formulation Aid" by Dow Corning, cetyl dimethicone copolyol, such as the product marketed under the trademark Abil EM 90R by Goldschmidt, and the mixture of cetyl dimethicone copolyol, of polyglycerol (4 mol) isostearate and of hexyl laurate marketed under the trademark Abil WE O9 by Goldschmidt. It is also possible to add thereto one or more coemulsifiers which, advantageously, can be selected from the group consisting of polyol alkyl esters.

Mention may in particular be made, as polyol alkyl esters, of polyethylene glycol esters, such as PEG-30 dipolyhydroxystearate, such as the product marketed under the trademark Arlacel P135 by ICI.

Mention may be made, as esters of glycerol and/or of sorbitan, for example, of polyglycerol isostearate, such as the product marketed under the trademark Isolan GI 34 by Goldschmidt; sorbitan isostearate, such as the product marketed under the trademark Arlacel 987 by ICI; glycerol sorbitan isostearate, such as the product marketed under the trademark Arlacel 986 by ICI, and their mixtures.

Mention may be made, for the O/W emulsions, for example, as emulsifiers, of nonionic emulsifiers, such as oxyalkylenated (more particularly polyoxyethylenated) esters of fatty acids and of glycerol; oxyalkylenated esters of fatty acids and of sorbitan; oxyalkylenated (oxyethylenated and/or oxypropylenated) fatty acid esters, such as the PEG-100 stearate/glyceryl stearate mixture marketed, for example, by ICI under the trademark Arlacel 165; oxyalkylenated (oxyethylenated and/or oxypropylenated) fatty alcohol ethers; sugar esters, such as sucrose stearate; ethers of fatty alcohol and of sugar, in particular alkyl polyglucosides (APG), such as decyl glucoside and lauryl glucoside, for example marketed by Henkel under the respective names Plantaren 2000 and Plantaren 1200, cetostearyl glucoside, optionally as a mixture with cetostearyl alcohol, for example marketed under the trademark Montanov 68 by Seppic, under the trademark Tegocare CG90 by Goldschmidt and under the trademark Emulgade KE3302 by Henkel, and arachidyl glucoside, for example in the form of the mixture of arachidyl and behenyl alcohols and of arachidyl glucoside marketed under the trademark Montanov 202 by Seppic. According to a specific embodiment of the invention, the mixture of the alkyl polyglucoside as defined above with the corresponding fatty alcohol can be in the form of a self-emulsifying composition, for example as disclosed in the WO-A-92/06778.

Use will more particularly be made, among other emulsion stabilizers, of polymers of isophthalic acid or sulfoisophthalic acid and in particular the phthalate/sulfoisophthalate/glycol copolymers, for example the diethyleneglycol/phthalate/iso-phthalate/1,4-cyclohexanedimethanol copolymer (INCI name: Polyester-5) marketed under the trademarks "Eastman AQ polymer" (AQ35S, AQ38S, AQ55S, AQ48 Ultra) by Eastman Chemical.

When an emulsion is involved, the aqueous phase thereof can comprise a nonionic vesicular dispersion prepared according to known methods (Bangham, Standish and Watkins, $J.\ Mol.\ Biol.$, 13, 238 (1965), FR 2 315 991 and FR 2 416 008).

The compositions according to the invention have applications in a large number of treatments, whether regime or regimen, in particular cosmetic/dermatological treatments, of the skin, the lips and the hair, including the scalp, in particular for protecting and/or caring for the skin, the lips and/or the hair, and/or for making up the skin and/or the lips.

The present invention also features the formulation of the compositions according to the invention into products for the cosmetic treatment of the skin, the lips, the nails, the hair, the eyelashes, the eyebrows and/or the scalp, in particular of care products, anti-sun/sunscreen products and makeup products.

The cosmetic compositions according to the invention can, for example, be makeup products.

The cosmetic compositions according to the invention can, for example, be used as a care product and/or anti-sun/sunscreen product for the face and/or the body with a liquid to semi-liquid consistency, such as milks, more or less smooth creams, cream gels or pastes. They can optionally be packaged in an aerosol and can be in the form of a foam or a spray.

The compositions according to the invention in the form of vaporizable fluid lotions in accordance with the invention are applied to the skin or the hair in the form of fine particles by means of pressurizing devices. The devices in accordance with the invention are well known to those skilled in the art and comprise non-aerosol pumps or "atomizers", the aerosol containers comprising a propellant and aerosol pumps using compressed air as propellant. The latter are described in U.S. Pat. Nos. 4,077,441 and 4,850,517.

The compositions packaged as an aerosol in accordance with the invention generally contain conventional propellants such as, for example, hydrofluorinated compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

In order to further illustrate the present invention and the advantages thereof, the following specific examples are given, it being understood that same are intended only as illustrative and in nowise limitative. In said examples to follow, all parts and percentages are given by weight, unless otherwise indicated.

SYNTHESIS EXAMPLES

Example 1

Preparation of 2,4-bis(ethyl 4'-diylaminobenzoate)-6-{[1,3,3,3-tetramethyl-1-[(trimethylsilyl)oxy]disiloxanyl]propyl-3-ylamino}-s-triazine

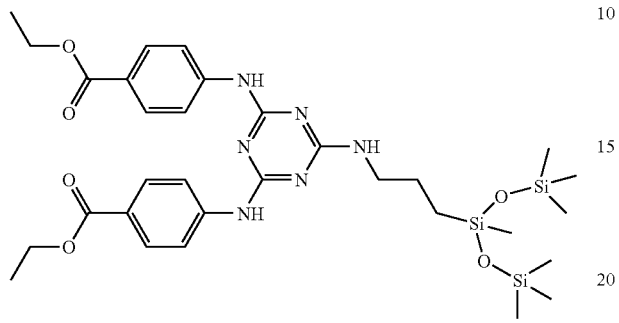

(a)

First Stage: Preparation of 2,4-dichloro-6-{[1,3,3,3-tetramethyl-1-[(trimethylsilyl)oxy]disiloxanyl]propyl-3-ylamino}-s-triazine:

Amino-1-[1,3,3,3-tetramethyl-1-[(trimethylsilyl)oxy]disiloxanyl]-3-propane (41.7 g, 0.149 mol) and a solution of sodium bicarbonate (11.4 g, 0.135 mol) in 120 ml of water are added, dropwise at 0° C., to a solution of cyanuryl chloride (25 g, 0.135 mol) in 250 ml of acetone, such that the pH is from 3 and 6.5. Once the introduction is complete, the pH is 6.5. Stirring is then maintained for 1 hour 30 minutes at 10° C. and the mixture is then left at laboratory temperature. The precipitate formed is filtered off, washed with water, spin-filter-dried and dried. 55.2 g (yield: 95%) of the expected derivative are obtained in the form of a white powder (Mp: 59° C.).

Second Stage: Preparation of the Derivative of Example 1:

The mixture of the above product (2.1 g, 0.005 mol) and of ethyl para-aminobenzoate (1.65 g, 0.01 mol) in suspension in 20 ml of toluene is refluxed for 1 hour 30 minutes. The mixture is cooled and hot heptane is added to the resin obtained. After trituration, filtration and drying, 2.3 g (yield: 67%) of the derivative of Example 1 are obtained in the form of a white powder:

Mp: 106-108° C.,
UV (ethanol): λmax=311 nm; E1%=1147.

Example 2

Preparation of 2,4-bis(n-butyl 4'-diylaminobenzoate)-6-{[1,3,3,3-tetramethyl-1-[(trimethylsilyl)oxy]disiloxanyl]propyl-3-ylamino}-s-triazine

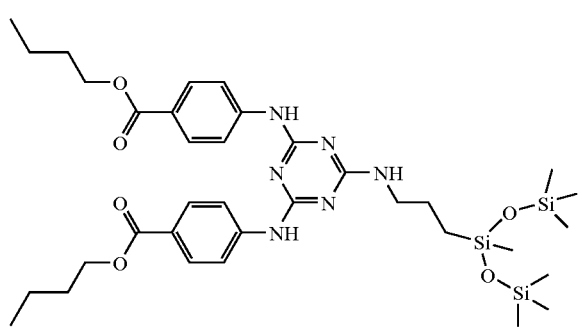

(b)

The mixture of the product of the first stage of Example 1 (16.74 g, 0.0391 mol), n-butyl para-aminobenzoate (15 g, 0.0776 mol) and potassium carbonate (5.36 g, 0.0388 mol) is suspended, under nitrogen sparging, in 170 ml of toluene and refluxed for 1 hour 20 minutes. The reaction mixture is cooled and 150 ml of dichloromethane are added thereto. The mineral products are filtered off. The filtrate is washed with bicarbonated water and twice with water. After drying of the organic phase and evaporation of the solvents, a white powder is obtained. After recrystallization from a 1:15 EtOAc/heptane mixture, 20.1 g (yield: 69%) of the derivative of Example 2 are obtained in the form of a white powder:

Mp: 111-113° C.,
UV (ethanol): λmax=312 nm; E1%=1055.

Example 3

Preparation of 2,4-bis(n-pentyl 4'-diylaminobenzoate)-6-{[1,3,3,3-tetramethyl-1-[(trimethylsilyl)oxy]disiloxanyl]propyl-3-ylamino}-s-triazine

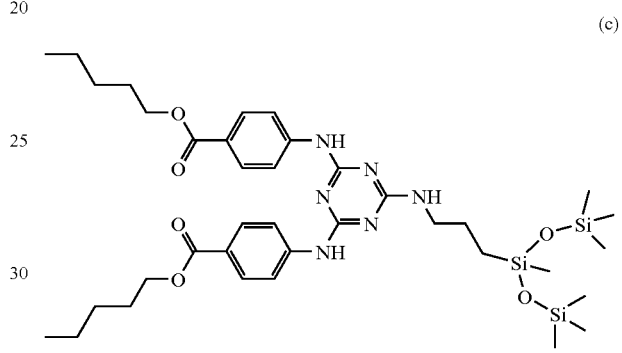

(c)

The mixture of the product of the first stage of Example 1 (1 g, 2.3×10$^{-3}$ mol), n-pentyl para-aminobenzoate (0.97 g, 4.6×10$^{-3}$ mol) and sodium bicarbonate (0.39 g, 4.6×10$^{-3}$ mol) in 15 ml of toluene is heated in a CEM Discover microwave apparatus for 20 minutes at a temperature of 115° C. and at a power of 150 watts. Dichloromethane is added to the reaction mixture and the subsequent mixture is washed with a saturated sodium chloride solution and then twice with water. After drying of the organic phase and evaporation of the solvents, a transparent oil is obtained. After purification on a silica column (eluent: 85:15 heptane/EtOAc), the clean fractions of the derivative of Example 3 are recovered (0.9 g, yield: 50%) in the form of a white powder:

UV (ethanol): λmax=312 nm; E1%=1008.

Example 4

Preparation of 2,4-bis[(1,1,3,3-tetramethylbutyl) 4'-diylaminobenzamide]-6-{[1,3,3,3-tetramethyl-1-[(trimethylsilyl)oxy]disiloxanyl]propyl-3-ylamino}-s-triazine

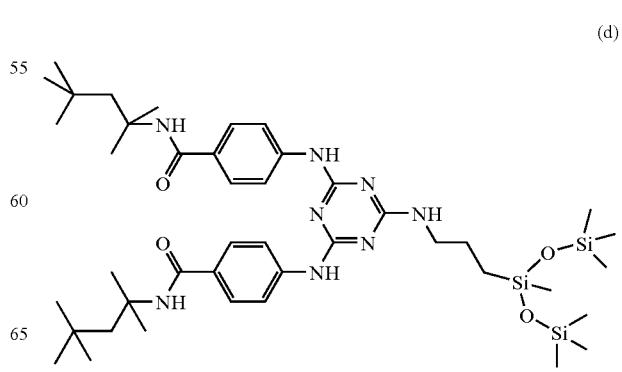

(d)

First Stage: Preparation of 4-nitro-N-(tert-octyl)benzamide:

tert-Octylamine (51.7 g, 0.4 mol) and triethylamine (61.2 ml, 0.44 mol) in 260 ml of dichloroethane are introduced into a reactor. The mixture is heated to 70° C. and then 4-nitrobenzoyl chloride (77.9 g, 0.42 mol) is added in small portions in 50 minutes. The mixture is refluxed for 4 hours. The reaction mixture is poured into ice-cold water; the product is extracted with dichloromethane, drying is carried out, and the solvent is evaporated off. The beige precipitate obtained is recrystallized from a mixture of isopropyl ether and ethanol (10:1 ratio). After drying under vacuum, 84.6 g (yield: 76%) of 4-nitro-N-(tert-octyl)benzamide are obtained in the form of an off-white powder, which is used as it is in the following stage.

Second Stage: Preparation of 4-amino-N-(tert-octyl)benzamide:

4-Nitro-N-(tert-octyl)benzamide (30 g, 0.108 mol) dissolved in 200 ml of ethyl acetate is hydrogenated, in a 500 ml hydrogenator, in the presence of 4.8 g of 10% palladium-on-charcoal containing 50% of water, as catalyst (hydrogen pressure: 8-10 bar), at a temperature of 70-75° C. for 1 hour and 15 minutes. After filtration, concentration of the solvent and drying under vacuum, 20.4 g (yield: 76%) of 4-amino-N-(tert-octyl)benzamide are obtained in the form of a light yellow powder, which is used as it is in the following stage.

Third Stage: Preparation of the Derivative of Example 4:

The mixture of the product of the first stage of Example 1 (1 g, $2.3 \times 10^{-3}$ mol), the product of the preceding stage (1.16 g, $4.6 \times 10^{-3}$ mol) and sodium bicarbonate (0.39 g, $4.6 \times 10^{-3}$ mol) in 10 ml of dry toluene is heated in a CEM Discover microwave apparatus for 20 minutes at a temperature of 115° C. and at a power of 150 watts. Dichloromethane is added to the reaction mixture and the subsequent mixture is washed with a saturated sodium chloride solution and then twice with water. After drying of the organic phase and evaporation of the solvents, a light yellow oil is obtained. After purification on a silica column (eluent: 70:30 heptane/EtOAc), the clean fractions of the derivative of Example 3 (0.9 g, yield: 45%) are recovered in the form of white flakes:

UV (ethanol): λmax=302 nm; E1%=775.

Example 5

Preparation of 2,4-bis(methyltrimethylsilyl 4'-diylaminobenzoate)-6-{[1,3,3,3-tetramethyl-1-[(trimethylsilyl)oxy]disiloxanyl]propyl-3-ylamino}-s-triazine

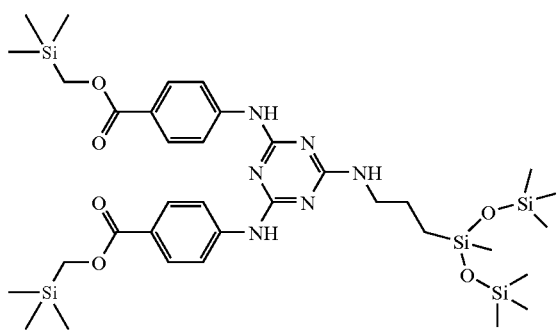

(e)

First Stage: Preparation of methyltrimethylsilyl 4-aminobenzoate:

Chloromethyltrimethylsilyl (38.5 g, 0.314 mol) is added dropwise at 80° C., in a reactor, to the heterogeneous mixture of the potassium salt of para-aminobenzoic acid (50 g, 0.285 mol) in 350 ml of DMF. The mixture is refluxed for 3 hours. After cooling, the salts are filtered and the DMF is evaporated off. The residue is taken up in dichloromethane and dried and the solvent is evaporated off. The oil obtained is purified by distillation. The fractions which distil at 189° C. under a vacuum of 0.6 mbar are recovered. The oil crystallizes. 50.4 g (yield: 79%) of the derivative of Example 5 are obtained in the form of a white powder, which is used as it is in the following stage.

Second Stage: Preparation of the Derivative of Example 5:

The mixture of the product of the first stage of Example 1 (2.1 g, $4.9 \times 10^{-3}$ mol) and the derivative of the preceding stage (2.19 g, $9.8 \times 10^{-3}$ mol) in 40 ml of toluene is refluxed for 5 hours, with nitrogen sparging. The mixture is cooled and the solvent is evaporated off. The residue is taken up in dichloromethane and dried and the solvent is evaporated off. 3 g (yield: 76%) of the derivative of Example 5 are obtained in the form of a pale yellow gum:

UV (ethanol): λmax=311 nm; E1%=907.

Example 6

Preparation of 2,4-bis(2-ethylhexyl 2'-hydroxy-4'-diylaminobenzoate)-6-{[1,3,3,3-tetramethyl-1-[(trimethylsilyl)oxy]disiloxanyl}propyl-3-ylamino}-s-triazine

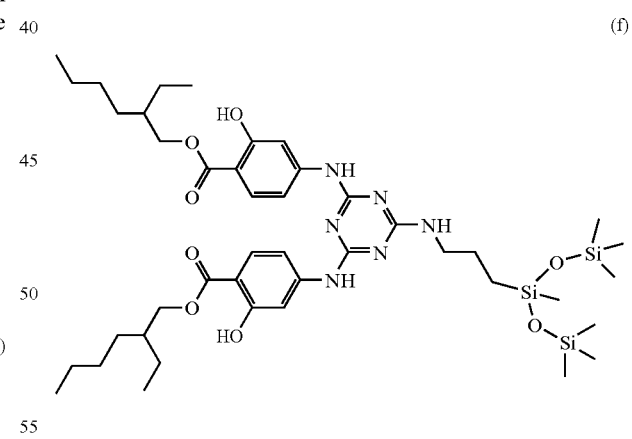

(f)

A mixture of 2-ethylhexyl 2-hydroxy-4-aminobenzoate (1.4 g, $5.57 \times 10^{-3}$ mol) and the product of the first stage of Example 1 (1.19 g, $2.78 \times 10^{-3}$ mol) in 10 ml of toluene is refluxed for 5 hours, with nitrogen sparging. The mixture is cooled and the solvent is evaporated off. The residue is chromatographed on a silica column (eluent: 9/1 heptane/EtOAc). 1.58 g (yield: 64%) of the clean fractions of the derivative of Example 6 are obtained in the form of a white paste:

UV (ethanol): λmax=300 nm; E1%=480.

λmax=325 nm, E1%=709.

Example 7

Preparation of the Random Derivative of Formula (Ia, III): $R_1$=n-butyl, X=O, n=0, B=A, W=H, Z=$CH_2$, $R_7$=$CH_3$, s=0, r=8.1

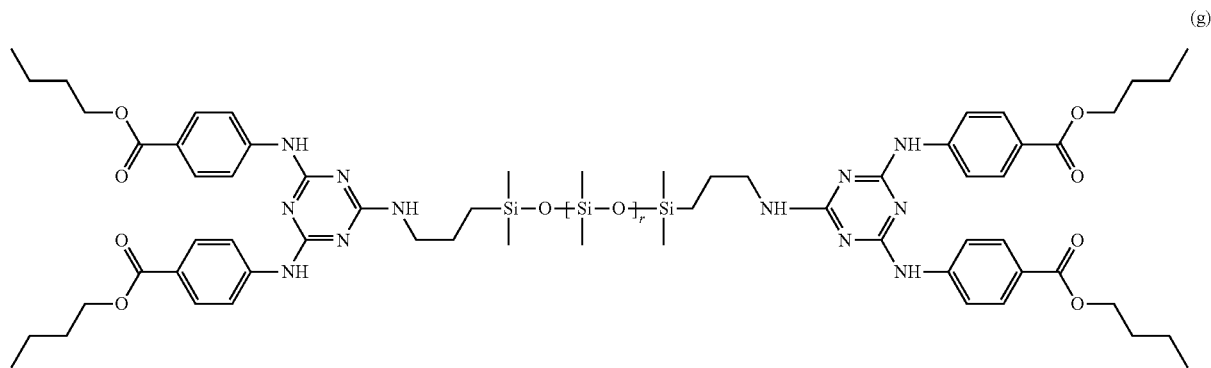

(g)

First Stage: Preparation of 2,4-bis(n-butyl 4'-diylaminobenzoate)-6-chloro-s-triazine:

n-Butyl para-aminobenzoate (113.94 g, 0.59 mol) and a solution of potassium carbonate (40.68 g, 0.295 mol) in 50 ml of water are added dropwise at 5° C. simultaneously to a solution of cyanuryl chloride (54.36 g, 0.295 mol) in 500 ml of dioxane and 50 ml of water, such that the pH is from 3 and 6.5. The mixture is maintained at 5° C. for 1 hour and 30 minutes. A precipitate forms in the medium and corresponds to the monosubstituted s-triazine. It is gradually heated to 70° C. and the second equivalent of potassium carbonate (40.68 g, 0.295 mol) is added in 50 ml of water. The stirring is then maintained for 5 hours at 70° C. The reaction mixture is cooled and filtered. The precipitate formed is washed with water, spin-filter-dried and dried. After recrystallization from dioxane/water, 52.5 g (yield: 36%) of the first recrystallization crop of 2,4-bis(n-butyl 4'-diylaminobenzoate)-6-chloro-s-triazine are obtained, after drying under vacuum, in the form of a white powder.

Second Stage: Preparation of the Derivative of Example 7:

A mixture of the preceding product (2 g, 4×10⁻³ mol), aminopropyl terminated polydimethylsiloxane (DMS-A-11 from Gelest) (2.13 g, 2×10⁻³ mol) and pyridine (0.32 ml, 4×10⁻³ mol) in 40 ml of toluene is heated at 70° C. for 5 hours, with nitrogen sparging. The mixture is cooled, dichloromethane is added, and the organic phase is washed 3 times with water. After drying of the organic phase and evaporation of the solvents, a brown oil is obtained. After treatment with carbon black in hot ethanol and filtration over Celite, 3.3 g (yield: 70%) of the derivative of Example 7 are obtained in the form of a light brown gum:

UV (ethanol): λmax=311 nm; E1%=916.

Example 8

Preparation of butyl 4-{[4-(butoxycarbonyl)phenyl]amino}-6-({3-[diethoxy(methyl)silyl]propyl}amino)-1,3,5-triazin-2-yl]amino}benzoate

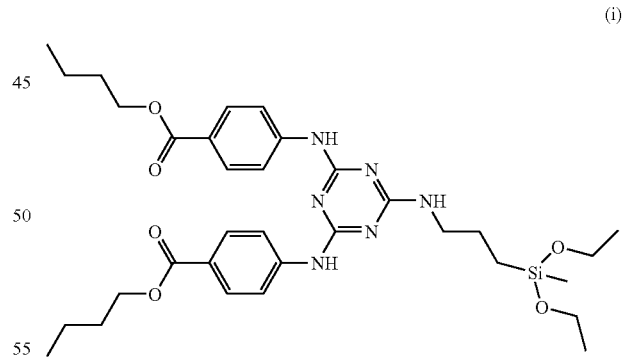

(i)

The heterogeneous mixture of the product of the first stage of Example 7 (20 g, 0.04 mol) and aminopropyldiethoxymethylsilane (15.37 g, 0.08 mol) is gradually heated to 70° C., with nitrogen sparging. After one hour, the mixture is cooled, dichloromethane is added, and the organic phase is washed 3 times with water. After drying of the organic phase and evaporation of the solvents, followed by recrystallization from heptane, 21 g (yield 80%) of a white solid of the derivative of Example 8 are obtained:

UV (ethanol): λmax=311 nm; E1%=1197.

Example 9

Preparation of the Random Derivative of Formula (Ia, III) Obtained by Polymerization of the Derivative of Example (8) with D5+MM: $R_1$=n-butyl, X=O, n=0, W=H, a=1, b=2, R=CH$_3$, Z=CH$_2$

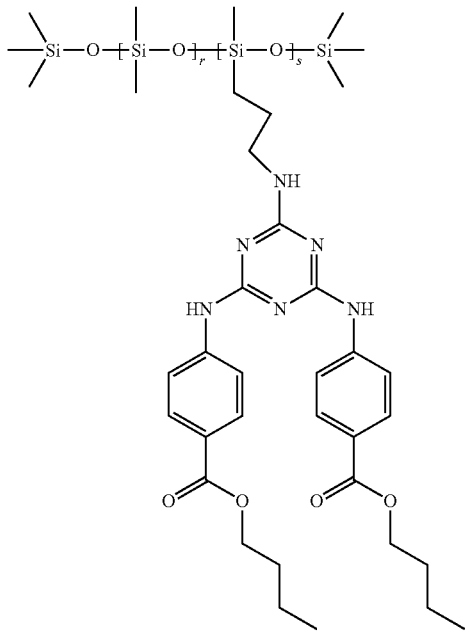

(h)

The heterogeneous mixture of the product of Example 8 (1 g, 1.53×10$^{-3}$ mol), decamethylcyclopentasiloxane (D5) (0.57 g, 1.53×10$^{-3}$ mol), hexamethyldisiloxane (MM) (0.062 g, 0.38×10$^{-3}$ mol) and concentrated hydrochloric acid (0.1 ml) is vigorously stirred, with nitrogen sparging, into a mixture of 10 ml of toluene and 1 ml of water. The mixture is gradually heated to 70° C. and left at this temperature for 2 hours. After cooling to ambient temperature and dilution with water, the whole is filtered. The precipitate obtained is washed with water and dried. 0.56 g of a white powder of the derivative of Example 9 is thus obtained:

UV (ethanol): λmax=311 nm; E1%=892.

Examples 10a and 10b

Preparation of the Derivatives: butyl 4-[(4-{[4-(butoxycarbonyl)phenyl]amino}-6-{(3-(1-hydroxy-1,3,3,3-tetramethyldisiloxanyl)propyl]amino}-1,3,5-triazin-2-yl)amino]benzoate and dibutyl 4,4'-{[6-({3-[dihydroxy(methyl)silyl]propyl}amino)-1,3,5-triazine-2,4-diyl]diimino}dibenzoate Obtained by Acid Treatment of the Derivative of Example (2)

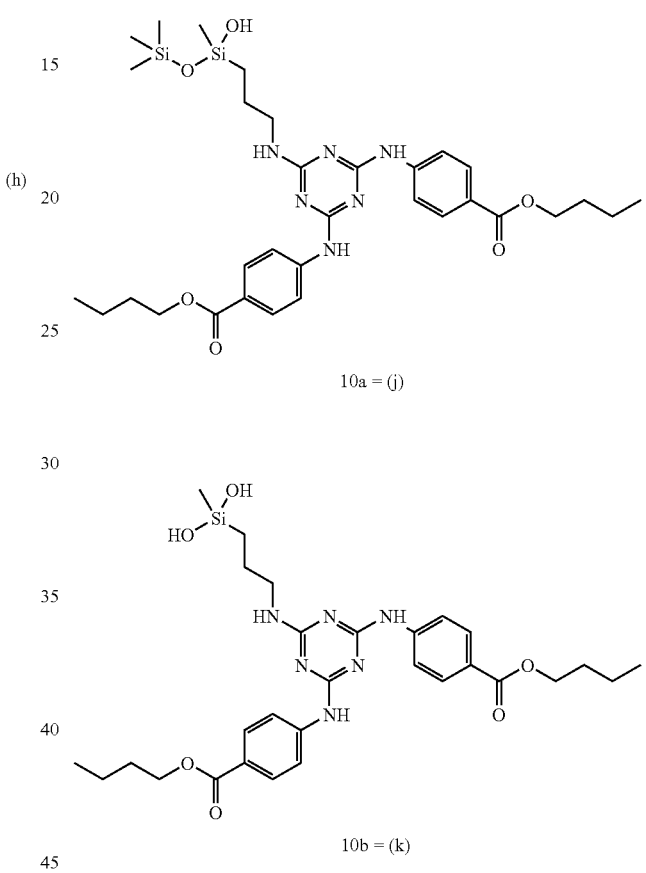

10a = (j)

10b = (k)

160 ml of 0.1N hydrochloric acid and 340 ml of an ethanol/isopropanol mixture in the ratio 80:20 are added to the derivative of Example 2 (10 g, 0.013 mol) solubilized in 500 ml of an ethanol/isopropanol mixture in the ratio 80:20. The mixture is left to stir at laboratory temperature for 5 hours. This solution is neutralized to pH 7 with 0.4% sodium hydroxide. 1 liter of water is added thereto and the solution is freeze-dried. The freeze-dried batches are combined to give 6.5 g of a light beige powder which contains, in relative percentages by HPLC, approximately 28% of the derivative of Example 10a and approximately 10% of the derivative of Example 10b. This powder was fractionated by centrifugal partition chromatography (with two-phase systems composed of heptane, ethyl acetate, methanol and water in various proportions) to give 0.58 g of the derivative of Example 10a in the form of a white powder:

UV (ethanol): λmax=312 nm; E1%=1228 and 0.42 g of the derivative of Example 10b in the form of a white powder.

Example 11

Preparation of the 7:93 Mixture of butyl 4-({4-{[4-(butoxycarbonyl)phenyl]amino}-6-[(2-{1,3,3,3-tetramethyl-1-[(trimethylsilyl)oxy]disiloxanyl}propyl)amino]-1,3,5-triazin-2-yl}amino)benzoate and 2,4-bis(ethyl 4'-diylaminobenzoate)-6-{[1,3,3,3-tetramethyl-1-[(trimethylsilyl)oxy]disiloxanyl]propyl-3-ylamino}-s-triazine

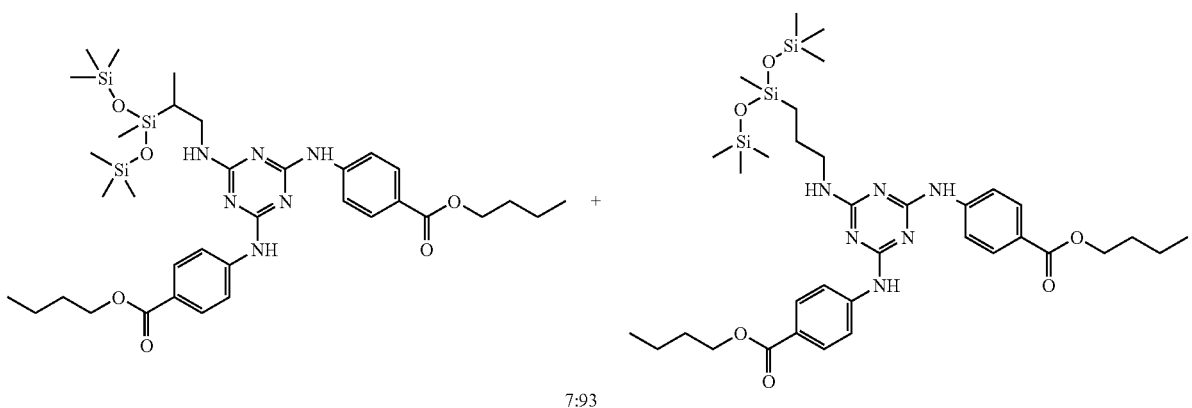 [SMILES: CCCCOC(=O)c1ccc(Nc2nc(NCC(C)[Si](C)(O[Si](C)(C)C)O[Si](C)(C)C)nc(Nc3ccc(C(=O)OCCCC)cc3)n2)cc1 ; CCCCOC(=O)c1ccc(Nc2nc(NCCC[Si](C)(O[Si](C)(C)C)O[Si](C)(C)C)nc(Nc3ccc(C(=O)OCCCC)cc3)n2)cc1]

7:93

A 7/93 mixture of 2-{1,3,3,3-tetramethyl-1-[(trimethylsilyl)oxy]disiloxanyl}propan-1-amine and 3-{1,3,3,3-tetramethyl-1-[(trimethylsilyl)oxy]disiloxanyl}propan-1-amine (30 g, 0.11 mol) is added, dropwise at 0° C. in 30 minutes, to a solution of cyanuryl chloride (19.8 g, 0.11 mol) and lutidine (11.5 g, 0.11 mol) in 100 ml of ethyl acetate. The mixture is left to stir at 0° C. for 30 minutes and then at 10° C. for 30 minutes and finally at 20° C. for 30 minutes. Pyridine (17.4 g, 0.22 mol) and n-butyl para-aminobenzoate (41.4 g, 0.22 mol) are then added and the mixture is heated at 70° C. for 3 hours. After cooling of the reaction mixture, the latter is washed with 2 times 100 ml of a saturated sodium chloride solution. This organic phase is passed over a bed of silica and the cake is rinsed with 80 ml of ethyl acetate. This organic phase is dried over sodium sulfate and the solvents are evaporated off. The residue obtained is crystallized from heptane. 50.2 g of a pale yellow solid are thus obtained. This solid is recrystallized from a 98:2 heptane/EtOAc mixture so as to obtain 49 g (yield: 60%) of the 7:93 mixture of the 2 isomers of Example 11 in the form of a white powder:

Mp: 165-167° C.,

UV (ethanol): $\lambda max$=312 nm; E1%=1040

Example 12

Preparation of the 50:50 Mixture of butyl 4-({4-{[4-(butoxycarbonyl)phenyl]amino}-6-[(2-{1,3,3,3-tetramethyl-1-[(trimethylsilyl)oxy]disiloxanyl}propyl)amino]-1,3,5-triazin-2-yl}amino)benzoate and 2,4-bis(ethyl 4'-diylaminobenzoate)-6-{[1,3,3,3-tetramethyl-1-[(trimethylsilyl)oxy]disiloxanyl]propyl-3-ylamino}-s-triazine

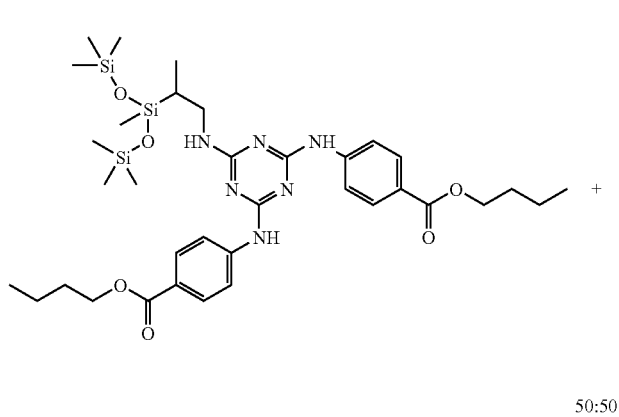

50:50

First Stage: Preparation of the 50:50 Mixture of 4,6-dichloro-N-(2-{1,3,3,3-tetramethyl-1-[(trimethylsilyl)oxy]disiloxanyl}propyl)-1,3,5-triazin-2-amine and 4,6-dichloro-N-(3-{1,3,3,3-tetramethyl-1-[(trimethylsilyl)oxy]disiloxanyl}propyl)-1,3,5-triazin-2-amine:

A 15/85 mixture of 2-{1,3,3,3-tetramethyl-1-[(trimethylsilyl)oxy]disiloxanyl}propan-1-amine and 3-{1,3,3,3-tetramethyl-1-[(trimethylsilyl)oxy]disiloxanyl}propan-1-amine (49.3 g, 0.176 mol) and a solution of sodium bicarbonate (14.8 g, 0.176 mol) in 210 ml of water are added, dropwise at 0° C., to a solution of cyanuryl chloride (32.5 g, 0.176 mol) in 180 ml of acetone, such that the pH is from 4 and 5.8. Once the introduction is complete, the pH is 5.3. Stirring is then maintained for 1 hour 30 minutes at 10° C. and the mixture is then left at laboratory temperature. The precipitate formed is filtered off, washed with water, spin-filter-dried and dried. 72.4 g (yield: 96%) of the expected isomeric derivatives, in the ratio 15/85, are obtained in the form of a white powder (Mp: 59° C.). A fractionation of 20 g of the preceding mixture over 2 successive chromatographic silica columns (eluent: 95:5 heptane/EtOAc) was carried out. It was possible to obtain 3.54 g of the 50:50 isomeric mixture, used as it is in the following stage.

Second Stage: Preparation of the Derivative of Example 12:

The mixture of the preceding product (3 g, 0.007 mol), n-butyl para-aminobenzoate (2.7 g, 0.014 mol) and sodium bicarbonate (1.18 g, 0.014 mol) in suspension in 30 ml of toluene is heated at 70° C. for 5 hours. The mixture is cooled and dichloromethane is added. After 2 washes with water, the organic phase is dried over sodium sulfate and the solvents are evaporated off. The residue obtained is crystallized from a 50:5 heptane/EtOAc mixture. The precipitate is then purified by means of a chromatographic silica column (eluent: 95:5 CH$_2$Cl$_2$/EtOAc) so as to obtain 3.7 g (yield: 71%) of the 50:50 mixture of the two isomers of Example 12 in the form of a white powder:

Mp: 165-167° C.,

UV (ethanol): λmax=312 nm; E1%=1149.

Example 13

Preparation of the Derivative of Formula (Ia, III):
$R_1$=n-butyl, X=O, n=0, B=CH$_3$, W=H, Z=CH$_2$, $R_7$=CH$_3$, S=1, r=0

(I)

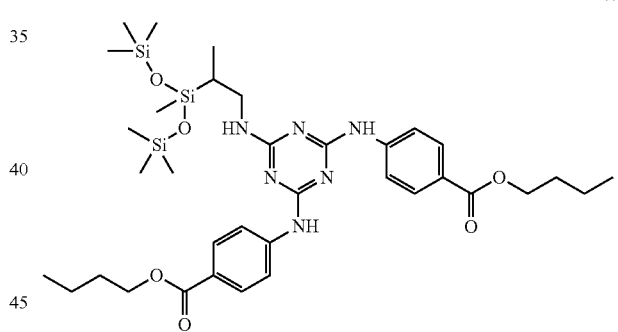

First Stage: Preparation of 4,6-dichloro-N-(2-{1,3,3,3-tetramethyl-1-[(trimethylsilyl)oxy]disiloxanyl}propyl)-1,3,5-triazin-2-amine:

The 15:85 isomeric mixture from the first stage of the synthesis of Example 12 was fractionated by centrifugal partition chromatography (two-phase system: 50:49:1 heptane/acetonitrile/water) so as to give 2.0 g of 4,6-dichloro-N-(2-{1,3,3,3-tetramethyl-1-[(trimethylsilyl)oxy]disiloxanyl}propyl)-1,3,5-triazin-2-amine, used as it is in the following stage:

Second Stage: Preparation of the Derivative of Example 13:

The preceding product (2 g, 0.0047 mol) is solubilized in 18 ml of toluene. Pyridine (0.8 ml, 0.009 mol) and n-butyl para-aminobenzoate (1.8 g, 0.009 mol) are added thereto. The mixture is heated at 70° C. for 3 hours with stirring. The solution is cooled and poured over a bed of silica, and the cake is rinsed with 80 ml of toluene. After evaporation of the solvent, the browny-beige solid obtained is crystallized from 30 ml of heptane. 2.2 g (yield: 63%) of the derivative of Example 13 are thus obtained in the form of a light beige powder:

Mp: 149-151° C.,

UV (ethanol): λmax=312 nm; E1%=955.

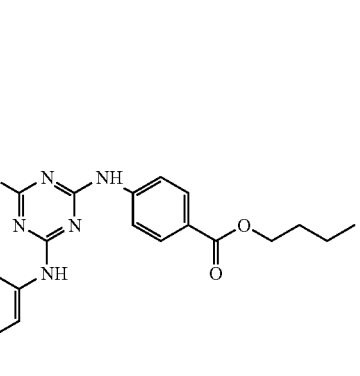

Example 14

Preparation of the Derivative of Formula (Ia, III):
$R_1$=n-butyl, X=O, n=0, B=$CH_3$, W=H, Z=$CH_2$,
$R_7$=$CH_3$, s=2, r=0

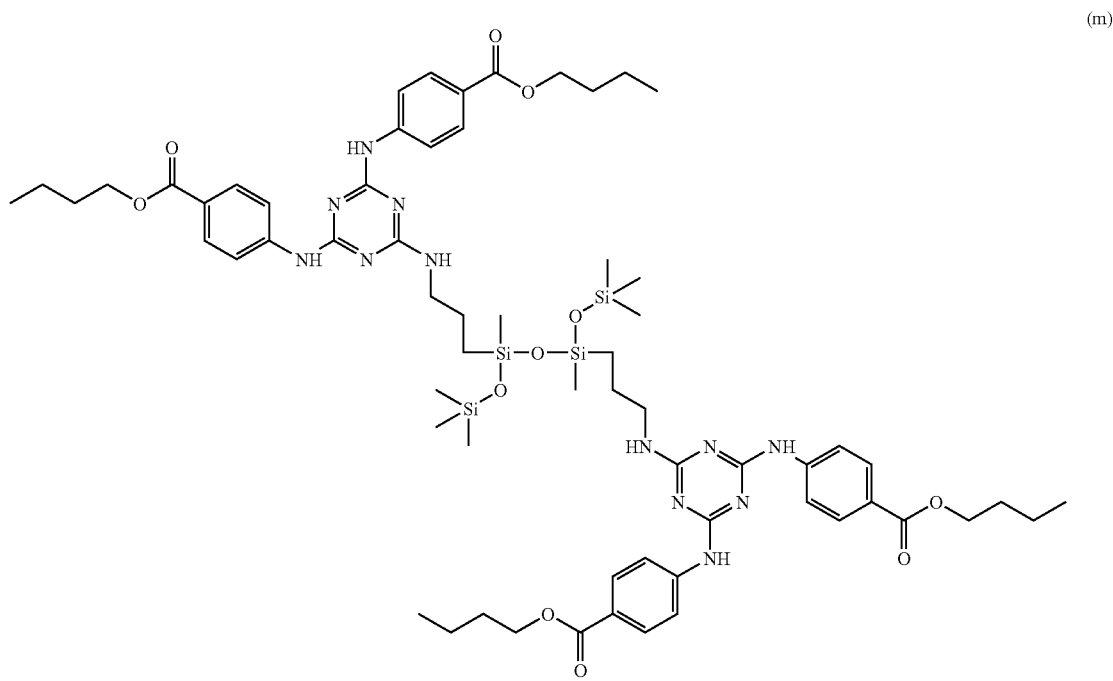 [SMILES: CCCCOC(=O)c1ccc(Nc2nc(NCCC[Si](C)(O[Si](C)(C)C)O[Si](C)(CCCNc3nc(Nc4ccc(C(=O)OCCCC)cc4)nc(Nc4ccc(C(=O)OCCCC)cc4)n3)O[Si](C)(C)C)nc(Nc3ccc(C(=O)OCCCC)cc3)n2)cc1]

(m)

25 ml of 1N hydrochloric acid are added to the derivative of Example 2 (1 g, 0.0013 mol) solubilized in 50 ml of an ethanol/isopropanol mixture in the ratio 80:20. The mixture is left to stand at laboratory temperature for 4 hours. This solution is neutralized to pH 7 with 35% sodium hydroxide. The solvents are evaporated off under vacuum. 0.8 g of a light beige powder is obtained, which contains, as relative percentage by HPLC, approximately 37% of the derivative of Example 14. This powder was fractionated by centrifugal partition chromatography (with a two-phase system composed of heptane, ethyl acetate, methanol and water) so as to give 0.18 g of the derivative of Example 14 in the form of a white powder:

UV (ethanol): λmax=312 nm; E1%=1109.

Formulation Examples 15 to 20

| Chemical name | Ex 15 | Ex 16 | Ex 17 |
|---|---|---|---|
| Phase A | | | |
| s-Triazine compound of Example 13 | 3 | | |
| s-Triazine compound of Example 2 | | 3 | |
| s-Triazine compound of Example 3 | | | 5 |
| Butylmethoxydibenzoylmethane (PARSOL 1789) | 2 | 2 | 2 |
| Bis-Ethylhexyloxyphenol Methoxyphenyl Triazine (Tinosorb S) | 3 | 3 | 3 |
| $C_{12}$-$C_{15}$ alkyl benzoate | 15 | 15 | 15 |
| Cetyl alcohol | 0.5 | 0.5 | 0.5 |
| Stearic acid | 1.5 | 1.5 | 1.5 |
| Mixture of glycerol monostearate/PEG stearate (100 EO) | 1 | 1 | 1 |
| Mixture of cetylstearyl glucoside and cetyl, stearyl alcohols | 2 | 2 | 2 |
| Dimethicone | 0.50 | 0.50 | 0.50 |
| Triethanolamine | 0.45 | 0.45 | 0.45 |
| Preservative agent | 1 | 1 | 1 |
| Titanium dioxide | | 5 | |
| Phase B | | | |
| Glycerol | 5 | 5 | 5 |
| Complexing agent | 0.1 | 0.1 | 0.1 |
| Monocetyl phosphate | 1 | 1 | 1 |
| Water | qs 100 G | qs 100 G | qs 100 G |
| Phase C | | | |
| Xanthan gum | 0.2 | 0.2 | 0.2 |
| Acrylic acid/stearyl methacrylate copolymer | 0.2 | 0.2 | 0.2 |
| Isohexadecane | 1 | 1 | 1 |
| Cyclopentasiloxane | | 1 | |
| Phase D | | | |
| Triethanolamine | qs pH | qs pH | qs pH |

| Chemical name | Ex 18 | Ex 19 | Ex 20 |
|---|---|---|---|
| Phase A | | | |
| s-Triazine compound of Example 13 | 3 | | |
| s-Triazine compound of Example 2 | | 3 | |
| s-Triazine compound of Example 3 | | | 5 |
| Butylmethoxydibenzoylmethane (PARSOL 1789) | 2 | 2 | 2 |
| 2,4,6-tris[p-(2'-ethylhexyl-1'-oxycarbonyl)anilino]-1,3,5-triazine (UVINUL T150) | 3 | 2 | 3 |
| $C_{12}$-$C_{15}$ alkyl benzoate | 15 | 15 | 15 |
| Cetyl alcohol | 0.5 | 0.5 | 0.5 |
| Stearic acid | 1.5 | 1.5 | 1.5 |
| Mixture of glyceryl monostearate/PEG stearate (100 EO) | 1 | 1 | 1 |
| Mixture of cetylstearyl glucoside and cetyl, stearyl alcohols | 2 | 2 | 2 |
| Dimethicone | 0.50 | 0.50 | 0.50 |
| Triethanolamine | 0.45 | 0.45 | 0.45 |
| Preservative agent | 1 | 1 | 1 |
| Titanium dioxide | | | 5 |
| Phase B | | | |
| Glycerol | 5 | 5 | 5 |
| Complexing agent | 0.1 | 0.1 | 0.1 |
| Monocetyl phosphate | 1 | 1 | 1 |
| Water | qs 100 G | qs 100 G | qs 100 G |
| Phase C | | | |
| Xanthan gum | 0.2 | 0.2 | 0.2 |
| Acrylic acid/stearyl methacrylate copolymer | 0.2 | 0.2 | 0.2 |
| Isohexadecane | 1 | 1 | 1 |
| Cyclopentasiloxane | | | 1 |
| Phase D | | | |
| Triethanolamine | qs pH | qs pH | qs pH |

Protocol:

The fatty phase (A) is heated to 70° C. The aqueous phase (B) is heated in the final beaker. Phase (C) is prepared: the powders are dispersed in oil. The fatty phase is emulsified in the aqueous phase with stirring using a rotor stator. Phase (C) is introduced with more vigorous stirring, and then the mixture is left to stir slowly until it is returned to ambient temperature. It is neutralized (D) and then packaged.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable, UV-photoprotective cosmetic/dermatological composition comprising:

(a) at least one silicon-containing s-triazine compound substituted with two aminobenzoate or aminobenzamide groups of formula (I) below or one of its tautomeric forms:

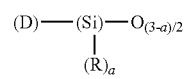

in which:

the radicals R, which may be identical or different, are each a linear or branched and optionally halogenated or unsaturated $C_1$-$C_{30}$ alkyl radical, a $C_6$-$C_{12}$ aryl radical, a $C_1$-$C_{10}$ alkoxy radical or the trimethylsilyloxy group;

a=0 to 3;

the group D is an s-triazine compound of formula (II) below:

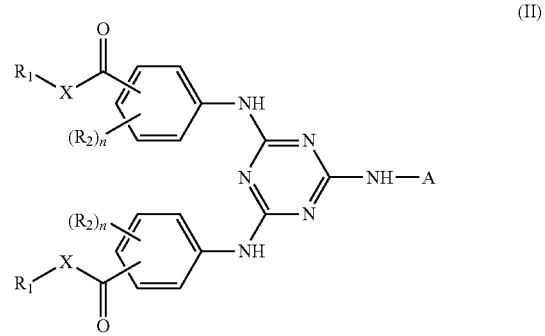

in which:

X is —O— or —NR$_3$—, in which R$_3$ is hydrogen or a $C_1$-$C_5$ alkyl radical, R$_1$ is a linear or branched and optionally unsaturated $C_1$-$C_{20}$ alkyl radical that may contain a silicon atom, a $C_5$-$C_{20}$ cycloalkyl radical optionally substituted with 1 to 3 linear or branched $C_1$-$C_4$ alkyl radicals, the —(CH$_2$CHR$_4$—O)$_m$R$_5$ group or the —CH$_2$—CH(OH)—CH$_2$—O—R$_6$ group, R$_4$ is hydrogen or methyl; with the proviso that the (C=O)XR$_1$ group is in the ortho-, meta- or para-position with respect to the amino group, R$_5$ is hydrogen or a $C_1$-$C_8$ alkyl radical, R$_6$ is hydrogen or a $C_4$-$C_8$ alkyl radical, m is an integer ranging from 2 to 20, n=0 to 2, the radicals R$_2$, which may be identical or different, are each a hydroxyl radical, a linear or branched $C_1$-$C_8$ alkyl radical, or a $C_1$-$C_8$ alkoxy radical, with the proviso that two adjacent radicals R$_2$ of the same aromatic ring may together form an alkylidenedioxy group in which the alkylidene group contains 1 or 2 carbon atoms, A is a divalent radical selected from among methylene, —[CH(Si(CH$_3$)$_3$]—, ethylene or a group corresponding to one of the following formulae (III), (IV) and (V):

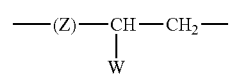

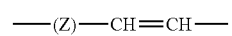

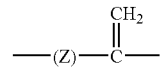

in which:
  Z is a linear or branched, saturated or unsaturated $C_1$-$C_{10}$ alkylene diradical optionally substituted with a hydroxyl radical or oxygen and that may optionally contain an amino group,
  W is a hydrogen atom, a hydroxyl radical or a linear or branched, saturated or unsaturated $C_1$-$C_8$ alkyl radical,
(b) at least one non-silicon-containing lipophilic 1,3,5-triazine compound UV-screening agent, formulated into a topically applicable, cosmetically/dermatologically acceptable support therefor.

2. The cosmetic/dermatological composition as defined by claim 1, in which the at least one compound of formula (I) is in the tautomeric form of formula (I') below:

(I')

in which the group D' is an s-triazine compound of formula (II') below:

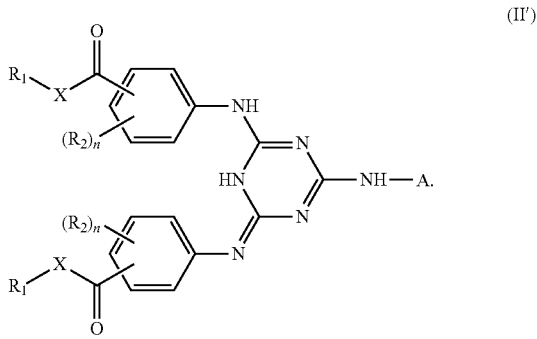

(II')

3. The cosmetic/dermatological composition as defined by claim 1, in which the at least one compound of formula (I) also comprises structural units of formula:

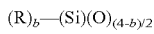

in which:
  R has the same definition as in formula (I),
  b=1, 2 or 3.

4. The cosmetic/dermatological composition as defined by claim 1, in which the at least one compound of formula (I) is/are selected from among those for which at least one of the following conditions are satisfied:
  R is methyl,
  $\underline{a}$=1 or 2,
  X is O,
  $R_1$ is a $C_4$-$C_5$ radical,
  n=0,
  the (C=O)$XR_1$ group is in the para-position with respect to the amino group,
  Z=—$CH_2$—, and
  W=H.

5. The cosmetic/dermatological composition as defined by claim 1, in which the at least one compound of formula (I) is/are selected from among those corresponding to one of the following formulae (Ia), (Ib) or (Ic):

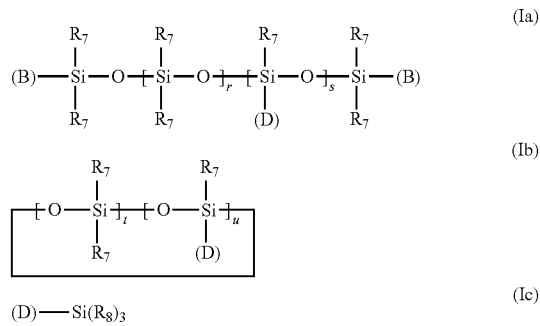

in which:
  (D) is as defined in formula (II),
  the radicals $R_7$, which may be identical or different, are each a linear or branched $C_1$-$C_{20}$ alkyl, phenyl, 3,3,3-trifluoropropyl or trimethylsilyloxy radical or the hydroxyl radical,
  the radicals $R_8$, which may be identical or different, are each a linear or branched $C_1$-$C_{20}$ alkyl or alkenyl radical, the hydroxyl radical or the phenyl radical,
  the radicals (B), which may be identical or different, are each a radical $R_7$ or a radical (D),
  r is an integer ranging from 0 to 200 inclusive,
  s is an integer ranging from 0 to 50, and if s=0, at least one of the two radicals (B) is (D),
  u is an integer ranging from 1 to 10,
  t is an integer ranging from 0 to 10, with the proviso that t+u is greater than or equal to 3, and also the tautomeric forms thereof.

6. The cosmetic/dermatological composition as defined by claim 5, in which the compounds of formula (Ia) or (Ib) are random polymers or oligomers having at least one of the following characteristics:
  $R_7$ is the methyl radical or the hydroxyl radical,
  B is methyl.

7. The cosmetic/dermatological composition as defined by claim 6, in which the at least compound of formula (I) is/are selected from among the compounds of formulae (a) to (m) below, and also the tautomeric forms thereof:

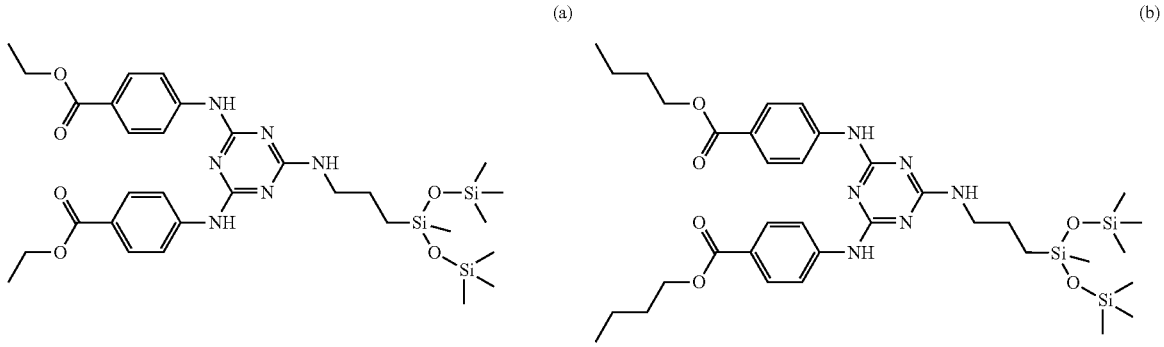

-continued
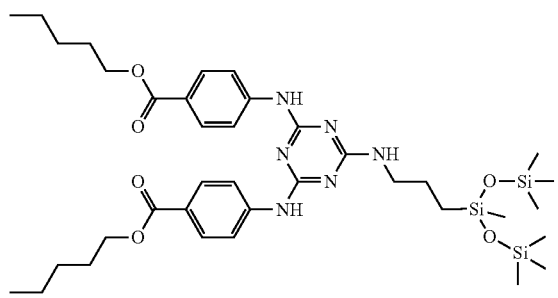
(c)
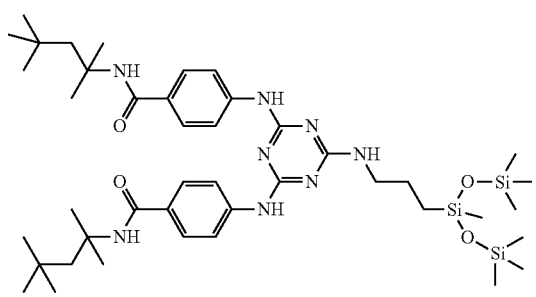
(d)
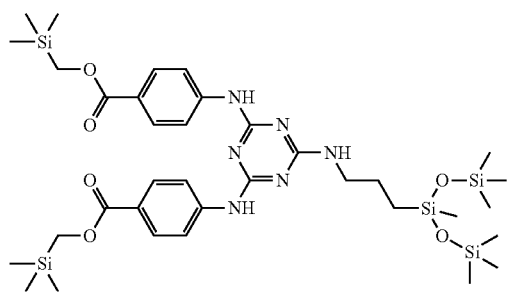
(e)
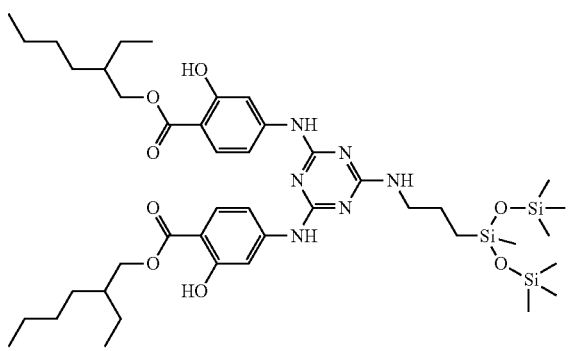
(f)
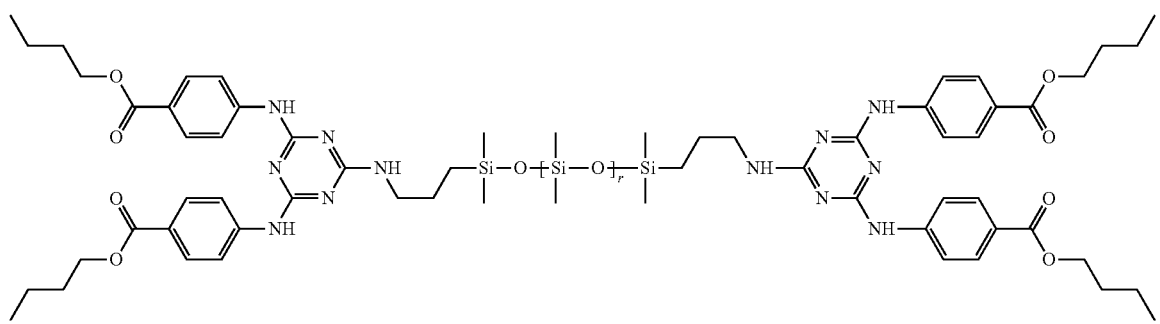
(g)
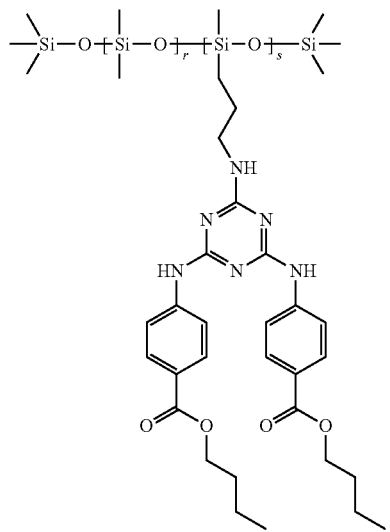
(h)
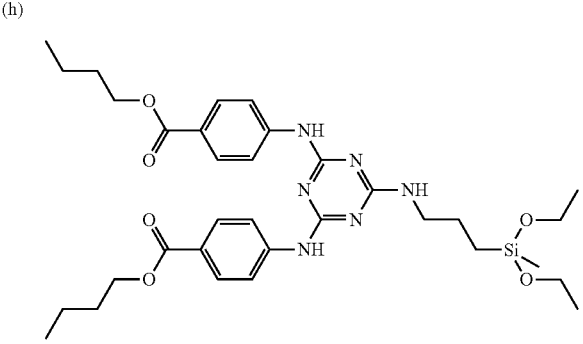
(i)

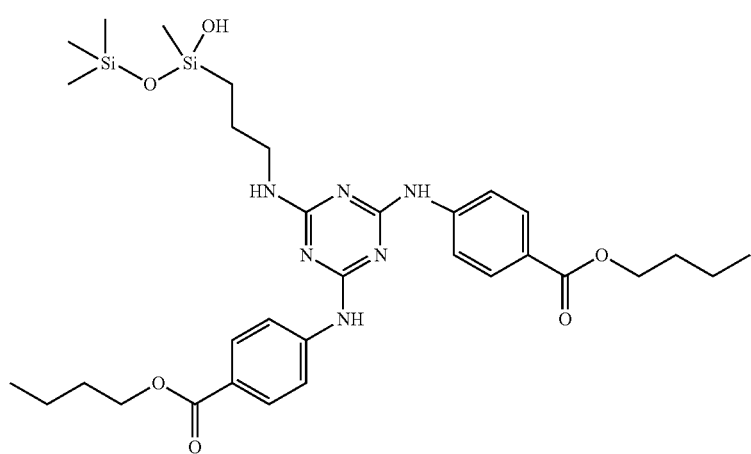
(j)
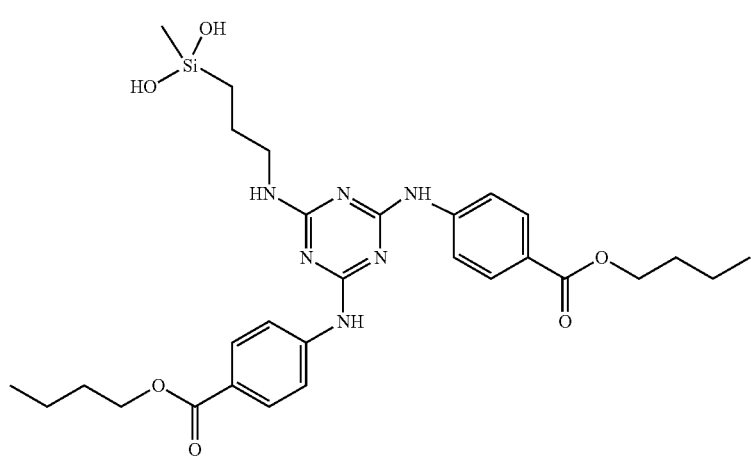
(k)
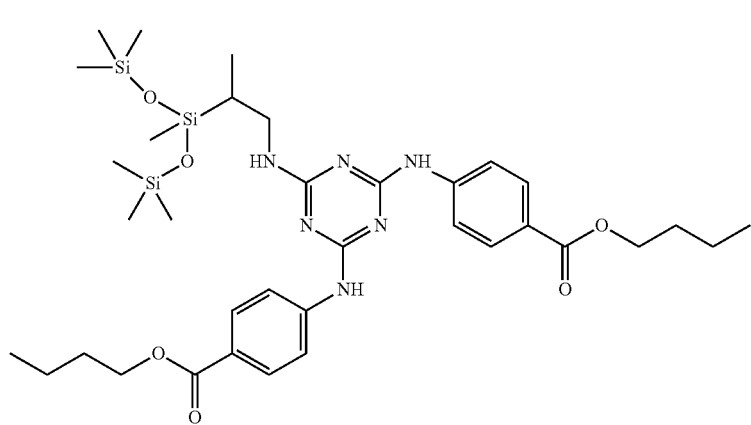
(l)

(m)

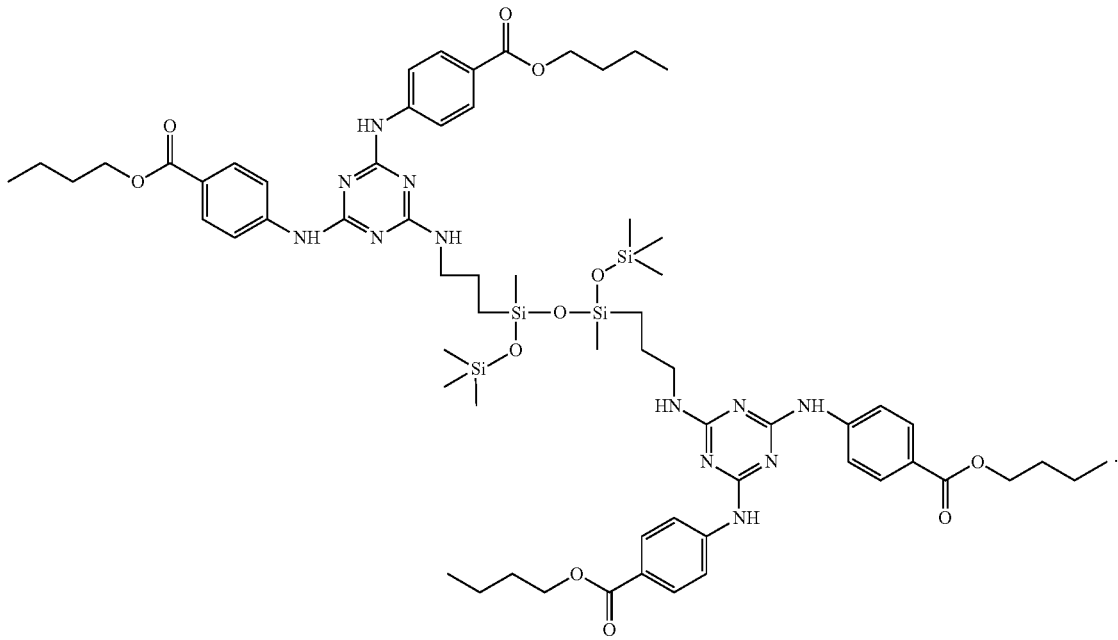

8. The cosmetic/dermatological composition as defined by claim 7, in which the at least one compound of formula (I) comprises the compound 2,4-bis(n-butyl 4'-diylaminobenzoate)-6-{[1,3,3,3-tetramethyl-1-[(trimethylsilyl)oxy]disiloxanyl]propyl-3-ylamino}-s-triazine of structure (b):

(b)

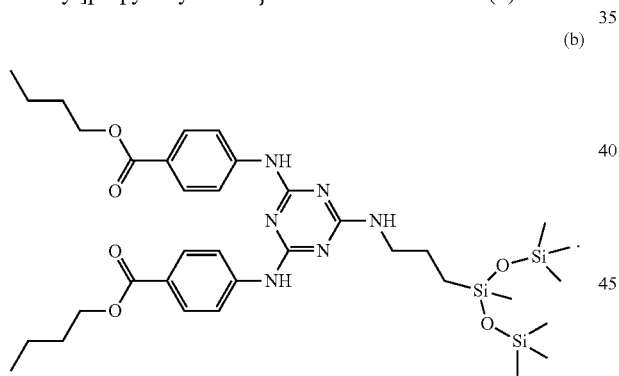

9. The cosmetic/dermatological composition as defined by claim 1, in which the at least one s-triazine compound of formula (I) is/are present at contents ranging from 0.01% to 20% by weight relative to the total weight of the composition.

10. The cosmetic/dermatological composition as defined by claim 1, in which the at least one non-silicon-containing lipophilic 1,3,5-triazine compound UV-screening agent is/are selected from among the 1,3,5-triazine compounds of formula (VIII) below:

(VIII)

in which the radicals $A_1$, $A_2$ and $A_3$, which may be identical or different, are each a group of formula (IX):

(IX)

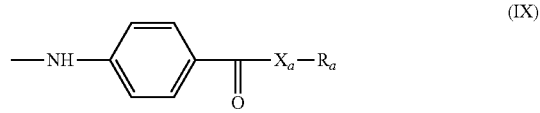

in which:

$X_a$, which may be identical or different, represent oxygen or the —NH— radical;

the radicals $R_a$, which may be identical or different, are each hydrogen; an alkali metal; an ammonium radical optionally substituted with one or more alkyl or hydroxyalkyl radicals; a linear or branched $C_1$-$C_{18}$ alkyl radical; a $C_5$-$C_{12}$ cycloalkyl radical optionally substituted with one or more $C_1$-$C_4$ alkyl radicals; a polyoxyethylenated radical comprising from 1 to 6 ethylene oxide units and the terminal OH group of which is methylated; a radical of formula (X), (XI) or (XII) below:

(X)

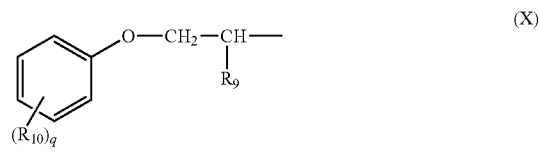

(XI)

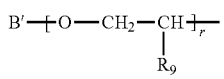

in which:

R$_9$ is hydrogen or a methyl radical;

R$_{10}$ is a C$_1$-C$_8$ alkyl radical;

q is an integer ranging from 0 to 3;

r is an integer ranging from 1 to 10;

A' is a C$_4$-C$_8$ alkyl radical or a C$_5$-C$_8$ cycloalkyl radical;

B' is selected from a linear or branched C$_1$-C$_8$ alkyl radical; a C$_5$-C$_8$ cycloalkyl radical; an aryl radical optionally substituted with one or more C$_1$-C$_4$ alkyl radicals.

11. The cosmetic/dermatological composition as defined by claim 10, in which the 1,3,5-triazine compounds of formula (VIII) are selected from among those in which A$_1$, A$_2$ and A$_3$ are of formula (IX) and have the following characteristics:

one of the X$_a$—R$_a$ radicals is the —NH—R$_a$ radical wherein R$_a$ is selected from among a C$_5$-C$_{12}$ cycloalkyl radical optionally substituted with one or more C$_1$-C$_4$ alkyl radicals; a radical of formula (X), (XI) or (XII) above in which B' is a C$_1$-C$_4$ alkyl radical and R$_{10}$ is the methyl radical;

the other two radicals X$_a$—R$_a$ are the —O—R$_a$ radical wherein the radicals R$_a$, which may be identical or different, are each hydrogen; an alkali metal; an ammonium radical optionally substituted with one or more alkyl or hydroxyalkyl radicals; a linear or branched C$_1$-C$_{18}$ alkyl radical; a C$_5$-C$_{12}$ cycloalkyl radical optionally substituted with one or more C$_1$-C$_4$ alkyl radicals; a radical of formula (X), (XI) or (XII) above in which B' is a C$_1$-C$_4$ alkyl radical and R$_{10}$ is the methyl radical.

12. The cosmetic/dermatological composition as defined by claim 10, in which the 1,3,5-triazine compounds of formula (VIII) are selected from among those in which A$_1$, A$_2$ and A$_3$ are of formula (IX) and have the following characteristics:

one or two radicals X$_a$—R$_a$ is/are the —NH—R$_a$ radical, wherein R$_a$ is selected from among a linear or branched C$_1$-C$_{18}$ alkyl radical; a C$_5$-C$_{12}$ cycloalkyl radical optionally substituted with one or more C$_1$-C$_4$ alkyl radicals; a radical of formula (X), (XI) or (XII) above in which B' is a C$_1$-C$_4$ alkyl radical and R$_5$ is the methyl radical;

the other or other two radicals X$_a$—R$_a$ is/are the —O—R$_a$ radical wherein the radicals R$_a$, which may be identical or different, are each hydrogen; an alkali metal; an ammonium radical optionally substituted with one or more alkyl or hydroxyalkyl radicals; a linear or branched C$_1$-C$_{18}$ alkyl radical; a C$_5$-C$_{12}$ cycloalkyl radical optionally substituted with one or more C$_1$-C$_4$ alkyl radicals; a radical of formula (X), (XI) or (XII) above in which B' is a C$_1$-C$_4$ alkyl radical and R$_5$ is the methyl radical.

13. The cosmetic/dermatological composition as defined by claim 12, in which the at least one 1,3,5-triazine compound of formula (VIII) comprises 2-[(p-(tert-butylamido)anilino]-4,6-bis[(p-(2'-ethylhexyl-1'-oxycarbonyl)anilino]-1,3,5-triazine corresponding to the following formula:

in which R''' is a 2-ethylhexyl radical and R'' is a tert-butyl radical.

14. The cosmetic/dermatological composition as defined by claim 10, in which said at least one 1,3,5-triazine compound of formula (VIII) is/are selected from among those for which A$_1$, A$_2$ and A$_3$ are of formula (IX) and have the following characteristics:

X$_a$ are identical and are oxygen;

the radicals R$_a$, which may be identical or different, are each a C$_6$-C$_{12}$ alkyl radical or a polyoxyethylenated radical having from 1 to 6 ethylene oxide units and the terminal OH group of which is methylated.

15. The cosmetic/dermatological composition as defined by claim 14, in which the at least one 1,3,5-triazine compound of formula (VIII) comprises 2,4,6-tris[p-(2'-ethylhexyl-t-oxycarbonyl)anilino]-1,3,5-triazine and corresponds to the following formula:

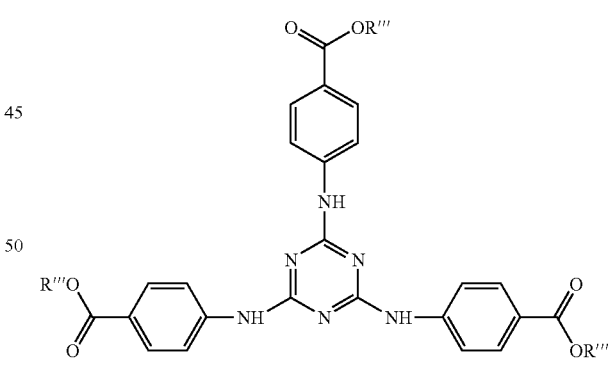

in which R''' is a 2-ethylhexyl radical.

16. The cosmetic/dermatological composition as defined by claim 1, in which said at least one non-silicon-containing lipophilic 1,3,5-triazine-type UV-screening agent comprises at least one bisresorcinyl triazine compound.

17. The cosmetic/dermatological composition as defined by claim 16, in which said at least one bisresorcinyl triazine compound is/are selected from among the compounds corresponding to formula (VIII) below:

(XIII)

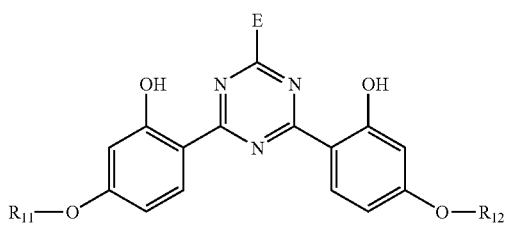

in which:
R$_{11}$ and R$_{12}$, which may be identical or different, are each a linear or branched C$_1$-C$_{30}$ alkyl radical or a linear or branched C$_2$-C$_{30}$ alkenyl radical,
E is a radical of formula (IX) or (X) below:

(XIV)

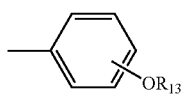

(XV)

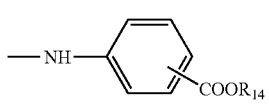

in which:
R$_{13}$ is hydrogen, a C$_1$-C$_{20}$ alkyl radical, the —(CH$_2$CHR$_{15}$—O)p-R$_{12}$ radical or the radical of formula —CH$_2$—CH(OH)—CH$_2$—O-T$_1$,
R$_{14}$ is hydrogen, a C$_1$-C$_{20}$ alkyl radical or a radical of formula —(CH$_2$)p-O-T$_1$,
R$_{15}$ is hydrogen or methyl,
T$_1$ is hydrogen or a C$_1$-C$_8$ alkyl radical,
o=1-16,
p=1-4.

18. The cosmetic/dermatological composition as defined by claim 17, in which said at least one bisresorcinyl triazine compound of formula (VIII) is/are selected from among the following compounds:
2,4-bis{[4-(2-ethylhexyloxy)-2-hydroxy]phenyl}-6-(4-methoxyphenyl)-1,3,5-triazine;
2,4-bis{[4-(3-(2-propyloxy)-2-hydroxypropyloxy)-2-hydroxy]phenyl}-6-(4-methoxyphenyl)-1,3,5-triazine;
2,4-bis{[4-(2-ethylhexyloxy)-2-hydroxy]phenyl}-6-[4-(2-methoxyethylcarboxyl)phenylamino]-1,3,5-triazine;
2,4-bis{[4-(2"-methylpropenyloxy)-2-hydroxy]phenyl}-6-(4-methoxyphenyl)-1,3,5-triazine;
2,4-bis{[4-(3-(2-propyloxy)-2-hydroxypropyloxy]-2-hydroxy]phenyl}-6-[(4-ethylcarboxyl)phenylamino]-1,3,5-triazine;
2,4-bis{[4-(2-ethylhexyloxy)-2-hydroxy]phenyl}-6-(1-methylpyrrol-2-yl)-1,3,5-triazine.

19. The cosmetic/dermatological composition as defined by claim 18, in which said at least one bisresorcinyl triazine compound of formula (VIII) comprises the compound 2,4-bis{[4-(2-ethylhexyloxy)-2-hydroxy]phenyl}-6-(4-methoxyphenyl)-1,3,5-triazine.

20. The cosmetic/dermatological composition as defined by claim 1, in which the at least one non-silicon-containing lipophilic 1,3,5-triazine compound UV-screening agent is/are present at contents ranging from 0.01% to 20% by weight relative to the total weight of the composition.

21. The cosmetic/dermatological composition as defined by claim 1, further comprising other organic or inorganic photoprotective agents that are active in the UV-A and/or UV-B range and that are water-soluble or liposoluble or insoluble in the conventional cosmetic solvents.

22. The cosmetic/dermatological composition as defined by claim 21, comprising additional organic photoprotective agents selected from among anthranilates; cinnamic derivatives; salicylic derivatives; camphor derivatives; benzophenone derivatives; β,β-diphenylacrylate derivatives; triazine derivatives; benzotriazole derivatives; benzalmalonate derivatives; benzimidazole derivatives; imidazolines; bis(benzoazolyl) derivatives; p-aminobenzoic acid (PABA) derivatives; methylene bis(hydroxyphenylbenzotriazole) derivatives; benzoxazole derivatives; screening polymers and screening silicones; -alkylstyrene-derived dimers; 4,4-diarylbutadienes and mixtures thereof.

23. The cosmetic/dermatological composition as defined by claim 22, comprising additional organic UV screening agent(s) selected from among the following compounds:
Ethylhexyl Methoxycinnamate;
Homosalate;
Ethylhexyl Salicylate;
Octocrylene;
Phenylbenzimidazole Sulfonic Acid;
Benzophenone-3;
Benzophenone-4;
Benzophenone-5;
n-Hexyl 2-(4-diethylamino-2-hydroxybenzoyl)benzoate;
4-Methylbenzylidene camphor;
Terephthalylidene Dicamphor Sulfonic Acid;
Disodium Phenyl Dibenzimidazole Tetrasulfonate;
Methylene bis-Benzotriazolyl Tetramethylbutylphenol;
Ethylhexyl triazone;
Bis-Ethylhexyloxyphenol Methoxyphenyl Triazine;
Diethylhexyl Butamido Triazone;
2,4,6-Tris(dineopentyl 4ÿ-aminobenzalmalonate)-s-triazine;
2,4,6-Tris(diisobutyl 4ÿ-aminobenzalmalonate)-s-triazine;
2,4,6-Tris(biphenyl-4-yl-1,3,5-triazine);
2,4,6-Tris(terphenyl)-1,3,5-triazine;
Drometrizole Trisiloxane;
Polysilicone-15;
Dineopentyl 4ÿ-methoxybenzalmalonate;
1,1-Dicarboxy-(2,2ÿ-dimethylpropyl)-4,4-diphenylbutadiene;
2,4-Bis[5-1(dimethylpropyl)benzoxazol-2-yl-(4-phenyl)-imino]-6-(2-ethylhexyl)-imino-1,3,5-triazine;
and mixtures thereof.

24. The cosmetic/dermatological composition as defined by claim 21, comprising additional inorganic photoprotective agents selected from among treated or untreated metal oxide pigments.

25. The cosmetic/dermatological composition as defined by claim 24, said pigments comprising treated or untreated titanium, zinc, iron, zirconium or cerium oxides and mixtures thereof.

26. The cosmetic/dermatological composition as defined by claim 1, further comprising at least one artificial tanning and/or browning agent for the skin.

27. The cosmetic/dermatological composition as defined by claim 1, further comprising at least one adjuvant selected from among fatty substances, organic solvents, ionic or non-ionic, hydrophilic or lipophilic thickeners, demulcents, humectants, opacifiers, stabilizers, emollients, silicones, anti-foaming agents, fragrances, preservatives, anionic, cationic, non-ionic, zwitterionic or amphoteric surfactants, active agents, fillers, polymers, propellants and basifying or acidifying agents.

28. The cosmetic/dermatological composition as defined by claim 1, formulated as an oil-in-water or water-in-oil emulsion.

29. The cosmetic/dermatological composition as defined by claim 1, formulated as a product for the cosmetic treatment of the skin, lips, nails, hair, eyelashes, eyebrows and/or scalp.

30. The cosmetic/dermatological composition as defined by claim 1, formulated as a care product for the skin, lips, nails, hair and/or scalp.

31. The cosmetic/dermatological composition as defined by claim 1, formulated as a makeup product.

\* \* \* \* \*